United States Patent
Becker et al.

(10) Patent No.: US 6,965,012 B1
(45) Date of Patent: Nov. 15, 2005

(54) FLINT POLYPEPTIDE ANALOGS

(75) Inventors: Gerald Wayne Becker, Fishers, IN (US); Fredric Jay Cohen, Newtown, PA (US); Patricia Ann Gonzalez-DeWhitt, Noblesville, IN (US); John Edward Hale, Fishers, IN (US); Radmila Micanovic, Indianapolis, IN (US); Christy Michelle Newton, Indianapolis, IN (US); Timothy Wayne Noblitt, Fishers, IN (US); Radhakrishnan Rathnachalam, Carmel, IN (US); Sheng-Hung Rainbow Tschang, Carmel, IN (US); Derrick Ryan Witcher, Fishers, IN (US); Victor John Wroblewski, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/936,024

(22) PCT Filed: Mar. 20, 2000

(86) PCT No.: PCT/US00/06417

§ 371 (c)(1),
(2), (4) Date: Sep. 7, 2001

(87) PCT Pub. No.: WO00/58465

PCT Pub. Date: Oct. 5, 2000

Related U.S. Application Data

(60) Provisional application No. 60/183,398, filed on Feb. 18, 2000, provisional application No. 60/160,566, filed on Oct. 20, 1999, provisional application No. 60/140,156, filed on Jun. 21, 1999, provisional application No. 60/140,077, filed on Jun. 21, 1999, and provisional application No. 60/126,839, filed on Mar. 30, 1999.

(51) Int. Cl.$^7$ .................. C07K 14/705; C07H 21/04
(52) U.S. Cl. ........................... 530/350; 536/23.5
(58) Field of Search ................. 530/350; 536/23.5

(56) References Cited

U.S. PATENT DOCUMENTS

| 5,194,596 A | * | 3/1993 | Tischer et al. ............... 530/399 |
| 5,350,836 A | * | 9/1994 | Kopchick et al. ............ 530/399 |
| 5,885,800 A | * | 3/1999 | Emery et al. ............... 435/69.1 |
| 2002/0150583 A1 | * | 10/2002 | Gentz et al. ............. 424/178.1 |

FOREIGN PATENT DOCUMENTS

| EP | 0 861 850 | * | 9/1998 |
| WO | WO 98/30694 | * | 7/1998 |
| WO | WO 99/04001 | | 1/1999 |
| WO | WO 99/07738 | * | 2/1999 |
| WO | WO 99/14330 | | 3/1999 |

OTHER PUBLICATIONS

Vukicevic et al., 1996, PNAS USA 93:9021–9026.*
Pitti et al., Nature, vol. 396, pp. 699–703, Dec., 1998.*
Pitti et al., Nature, vol. 396, pp. 699–703, Dec., 1998.*

* cited by examiner

*Primary Examiner*—Lorraine Spector
*Assistant Examiner*—Eileen B. O'Hara
(74) *Attorney, Agent, or Firm*—Thomas D. Webster

(57) ABSTRACT

Disclosed are polypeptide analogs of FLINT, polydeoxynucleotides encoding FLINT analogs, and methods of using FLINT analogs and polydeoxynucleotides. The FLINT analogs of the invention include polypeptides having the amino acid sequence of FLINT, modified at one or more positions with amino acid substitutions, and include fragments thereof, as well as Fc fusions comprising FLINT and FLINT analogs.

6 Claims, 2 Drawing Sheets

SEQUENCE LISTING

```
<160> NUMBER OF SEQ ID NOS: 4

<210> SEQ ID NO 1
<211> LENGTH: 271
<212> TYPE: PRT
<213> ORGANISM: Homo sapiens

<400> SEQUENCE: 1

Val Ala Glu Thr Pro Thr Tyr Pro Trp Arg Asp Ala Glu Thr Gly Glu
  1               5                  10                  15

Arg Leu Val Cys Ala Gln Cys Pro Pro Gly Thr Phe Val Gln Arg Pro
             20                  25                  30

Cys Arg Arg Asp Ser Pro Thr Thr Cys Gly Pro Cys Pro Pro Arg His
         35                  40                  45

Tyr Thr Gln Phe Trp Asn Tyr Leu Glu Arg Cys Arg Tyr Cys Asn Val
     50                  55                  60
```

```
Leu Cys Gly Glu Arg Glu Glu Ala Arg Ala Cys His Ala Thr His
 65                  70                  75                  80

Asn Arg Ala Cys Arg Cys Arg Thr Gly Phe Phe Ala His Ala Gly Phe
                 85                  90                  95

Cys Leu Glu His Ala Ser Cys Pro Pro Gly Ala Gly Val Ile Ala Pro
            100                 105                 110

Gly Thr Pro Ser Gln Asn Thr Gln Cys Gln Pro Cys Pro Gly Thr
        115                 120                 125

Phe Ser Ala Ser Ser Ser Ser Glu Gln Cys Gln Pro His Arg Asn
    130                 135                 140

Cys Thr Ala Leu Gly Leu Ala Leu Asn Val Pro Gly Ser Ser Ser His
145                 150                 155                 160

Asp Thr Leu Cys Thr Ser Cys Thr Gly Phe Pro Leu Ser Thr Arg Val
                165                 170                 175

Pro Gly Ala Glu Glu Cys Glu Arg Ala Val Ile Asp Phe Val Ala Phe
            180                 185                 190

Gln Asp Ile Ser Ile Lys Arg Leu Gln Arg Leu Leu Gln Ala Leu Glu
        195                 200                 205

Ala Pro Glu Gly Trp Gly Pro Thr Pro Arg Ala Gly Arg Ala Ala Leu
    210                 215                 220

Gln Leu Lys Leu Arg Arg Arg Leu Thr Glu Leu Leu Gly Ala Gln Asp
225                 230                 235                 240

Gly Ala Leu Leu Val Arg Leu Leu Gln Ala Leu Arg Val Ala Arg Met
                245                 250                 255

Pro Gly Leu Glu Arg Ser Val Arg Glu Arg Phe Leu Pro Val His
            260                 265                 270

<210> SEQ ID NO 2
<211> LENGTH: 813
<212> TYPE: DNA
<213> ORGANISM: Homo sapiens

<400> SEQUENCE: 2
gtggcagaaa cacccaccta cccctggcgg gacgcagaga caggggagcg gctggtgtgc    60
gcccagtgcc ccccaggcac ctttgtgcag cggccgtgcc gccgagacag ccccacgacg   120
tgtggcccgt gtccaccgcg ccactacacg cagttctgga actacctgga gcgctgccgc   180
tactgcaacg tcctctgcgg ggagcgtgag gaggaggcac gggcttgcca cgccacccac   240
aaccgtgcct gccgctgccg caccggcttc ttcgcgcacg ctggtttctg cttggagcac   300
gcatcgtgtc cacctggtgc cggcgtgatt gccccgggca cccccagcca gaacacgcag   360
tgccagccgt gcccccagg caccttctca gccagcagct ccagctcaga gcagtgccag   420
ccccaccgca actgcacggc cctgggcctg gccctcaatg tgccaggctc ttcctcccat   480
gacaccctgt gcaccagctg cactggcttc cccctcagca ccagggtacc aggagctgag   540
gagtgtgagc gtgccgtcat cgactttgtg gctttccagg acatctccat caagaggctg   600
cagcggctgc tgcaggccct cgaggccccg gagggctggg gtccgacacc aagggcgggc   660
cgcgcggcct tgcagctgaa gctgcgtcgg cggctcacgg agctcctggg ggcgcaggac   720
ggggcgctgc tggtgcggct gctgcaggcg ctgcgcgtgg ccaggatgcc cgggctggag   780
cggagcgtcc gtgagcgctt cctccctgtg cac                                 813

<210> SEQ ID NO 3
<211> LENGTH: 300
```

```
<212> TYPE: PRT
<213> ORGANISM: Homo sapiens

<400> SEQUENCE: 3

Met Arg Ala Leu Glu Gly Pro Gly Leu Ser Leu Leu Cys Leu Val Leu
  1               5                  10                  15

Ala Leu Pro Ala Leu Leu Pro Val Pro Ala Val Arg Gly Val Ala Glu
             20                  25                  30

Thr Pro Thr Tyr Pro Trp Arg Asp Ala Glu Thr Gly Glu Arg Leu Val
         35                  40                  45

Cys Ala Gln Cys Pro Pro Gly Thr Phe Val Gln Arg Pro Cys Arg Arg
 50                  55                  60

Asp Ser Pro Thr Thr Cys Gly Pro Cys Pro Arg His Tyr Thr Gln
 65                  70                  75                  80

Phe Trp Asn Tyr Leu Glu Arg Cys Arg Tyr Cys Asn Val Leu Cys Gly
                 85                  90                  95

Glu Arg Glu Glu Glu Ala Arg Ala Cys His Ala Thr His Asn Arg Ala
                100                 105                 110

Cys Arg Cys Arg Thr Gly Phe Phe Ala His Ala Gly Phe Cys Leu Glu
            115                 120                 125

His Ala Ser Cys Pro Pro Gly Ala Gly Val Ile Ala Pro Gly Thr Pro
130                 135                 140

Ser Gln Asn Thr Gln Cys Gln Pro Cys Pro Pro Gly Thr Phe Ser Ala
145                 150                 155                 160

Ser Ser Ser Ser Ser Glu Gln Cys Gln Pro His Arg Asn Cys Thr Ala
                165                 170                 175

Leu Gly Leu Ala Leu Asn Val Pro Gly Ser Ser Ser His Asp Thr Leu
            180                 185                 190

Cys Thr Ser Cys Thr Gly Phe Pro Leu Ser Thr Arg Val Pro Gly Ala
            195                 200                 205

Glu Glu Cys Glu Arg Ala Val Ile Asp Phe Val Ala Phe Gln Asp Ile
210                 215                 220

Ser Ile Lys Arg Leu Gln Arg Leu Leu Gln Ala Leu Glu Ala Pro Glu
225                 230                 235                 240

Gly Trp Gly Pro Thr Pro Arg Ala Gly Arg Ala Ala Leu Gln Leu Lys
                245                 250                 255

Leu Arg Arg Arg Leu Thr Glu Leu Leu Gly Ala Gln Asp Gly Ala Leu
            260                 265                 270

Leu Val Arg Leu Leu Gln Ala Leu Arg Val Ala Arg Met Pro Gly Leu
            275                 280                 285

Glu Arg Ser Val Arg Glu Arg Phe Leu Pro Val His
            290                 295                 300

<210> SEQ ID NO 4
<211> LENGTH: 29
<212> TYPE: PRT
<213> ORGANISM: Homo sapiens

<400> SEQUENCE: 4

Met Arg Ala Leu Glu Gly Pro Gly Leu Ser Leu Leu Cys Leu Val Leu
  1               5                  10                  15

Ala Leu Pro Ala Leu Leu Pro Val Pro Ala Val Arg Gly
             20                  25
```

FLINT POLYPEPTIDE ANALOGS

CROSS-REFERENCE

Figure 1:
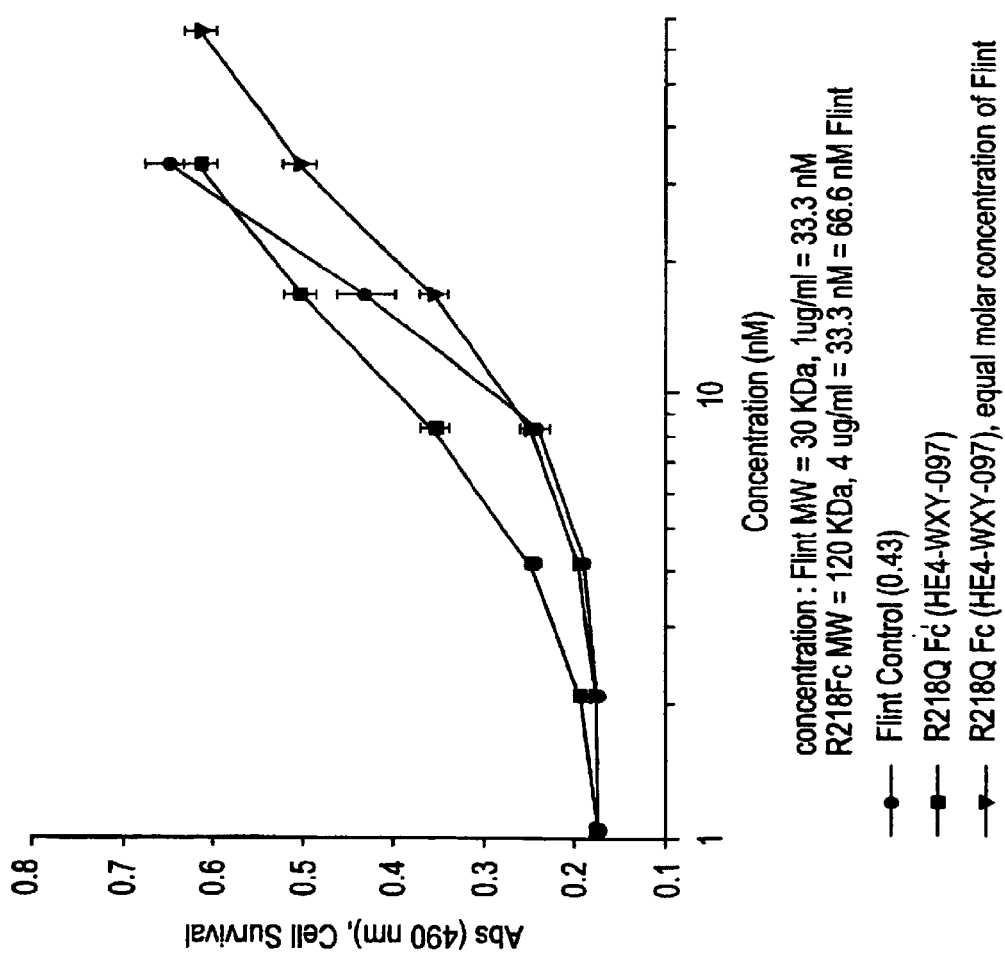
Figure 2:
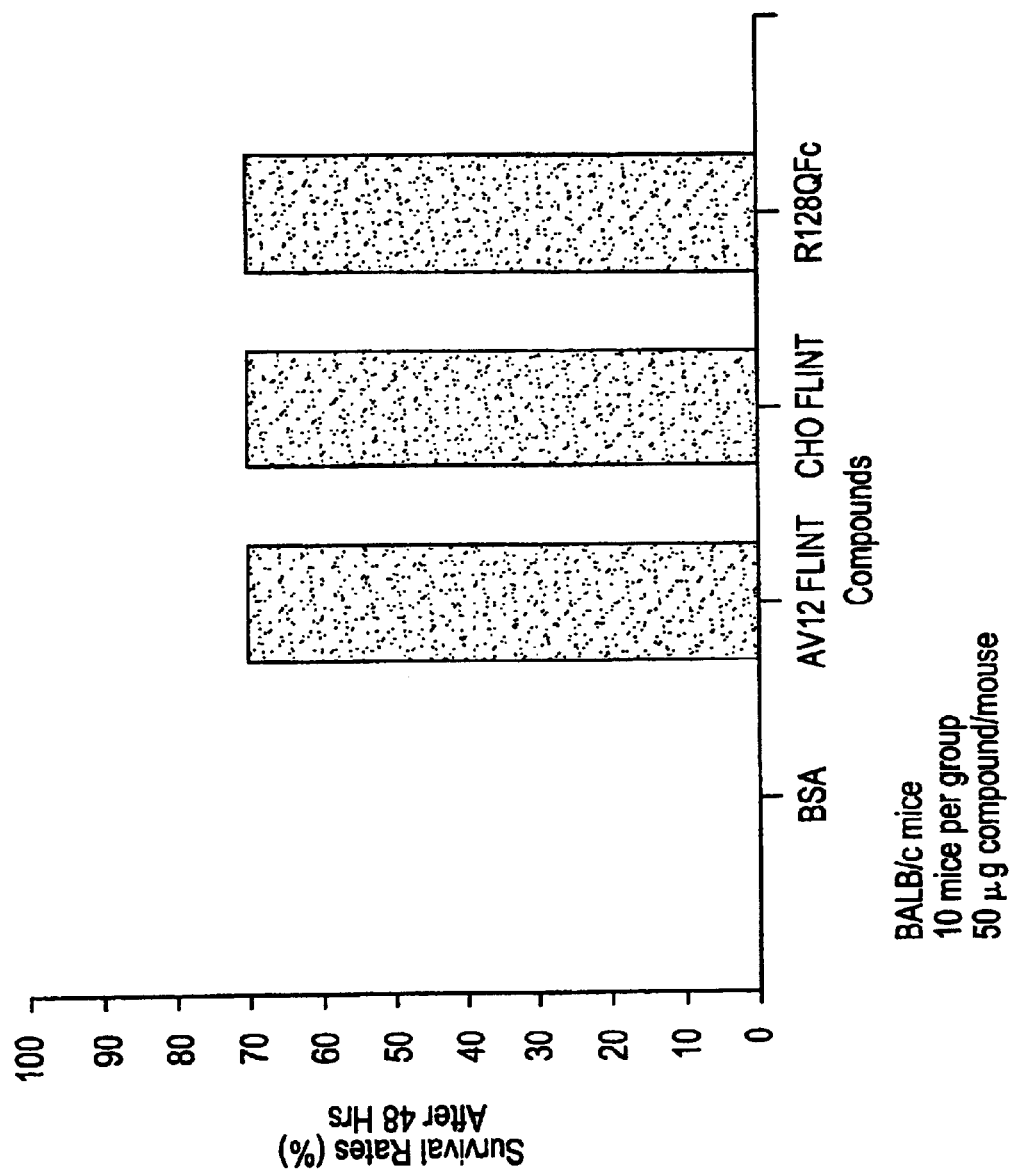

This application claims the benefit of U.S. Provisional Application Nos. 60/126,839, filed Mar. 30, 1999; 60/140,077, filed Jun. 21, 1999; 60/140,156, filed Jun. 21, 1999; 60/160,566, filed Oct. 20, 1999; and No. 60/183,398 filed Feb. 18, 2000.

BACKGROUND OF THE INVENTION

A number of tumor necrosis factor receptor proteins ("TNFR proteins") and proteins homologous thereto have been isolated in recent years. They have many potent biological effects and aberrant activity of these proteins has been implicated in a number of disease states.

One such TNFR homologue, reported in July, 1998 (Gentz et al., WO 98/30694), binds the protein FAS Ligand and thereby inhibits the activation of another TNFR homologue, FAS, by FAS Ligand (U.S. Provisional Applications Ser. Nos. 60/112,577, 60/112,933, and 60/113,407, filed Dec. 17, 18 and 22, 1998, respectively; the entire teachings of these applications are incorporated herein by reference).

This new protein is referred to herein as "FAS Ligand Inhibitory Protein" or "FLINT".

Over activation of FAS by FAS Ligand has been implicated in a number of pathological conditions, including runaway apoptosis (Kondo et al., Nature Medicine 3(4): 409–413 (1997) and Galle et al., *J. Exp. Med.* 182:1223–1230 (1995)) and inflammatory disease resulting from neutrophil activation (Miwa et al.,. Nature Medicine 4:1287 (1998)).

"Runaway apoptosis" is a level of apoptosis greater than normal, or apoptosis occurring at an inappropriate time. Pathological conditions caused by runaway apoptosis include, organ failure, for example, in the liver, kidneys and pancreas. Inflammatory diseases associated with excessive neutrophil activation include, but are not limited to, sepsis, ARDS, SIRS and MODS.

Compounds such as FLINT which inhibit the binding of FAS to FAS Ligand, or LIGHT to LTβR and/or TR2/HVEM receptors can be used to treat or prevent diseases or conditions that are mechanistically-linked to these binding interactions. However, the potential of FLINT as a useful therapeutic is dependent, at least in part, on the development of analogs with improved pharmacological properties (e.g., greater potency, longer in vivo half-lives and greater affinity for FAS Ligand) and/or improved pharmaceutical properties (e.g., decreased aggregation and surface absorption properties and increased solubility and ease of formulation).

SUMMARY OF THE INVENTION

The present invention relates to polypeptide analogs of FLINT, polydeoxynucleotides encoding the FLINT analogs, and methods of using the polypeptide analogs and polydeoxynucleotides. FLINT analogs disclosed herein include polypeptides having the amino acid sequence of FLINT, modified at one or more positions with amino acid substitutions, deletions, or additions (hereinafter "modified FLINT polypeptides"), and fragments thereof (hereinafter "modified FLINT polypeptide fragments"). The analogs of FLINT disclosed herein are believed to have improved properties compared with FLINT. Examples of improved properties include greater potency, longer in vivo half-lives, decreased aggregation, decreased absorption onto surfaces, increased solubility and improved ease of formulation. Improved potency can be assessed by the binding assay described in Example 13; improved pharmaceutical properties can be assessed by the assays described in Example 10.

One embodiment of the present invention relates to analogs comprising a modified FLINT polypeptide or a fragment thereof.

In one aspect, the modified FLINT polypeptide comprises hydrophobic to hydrophilic substitutions having an amino acid sequence of SEQ ID NO:1, modified by:
  a) replacing tryptophan at position 53 with aspartic acid;
  b) replacing threonine at position 88 with proline;
  c) replacing alanine at position 107 with serine, aspartic acid, glutamic acid or threonine;
  d) replacing isoleucine at position 110 with threonine or glutamic acid; or
  e) replacing proline at position 104 with serine.

In another aspect, the modified FLINT polypeptide comprising new glycosylation sites having an amino acid sequence of SEQ ID NO:1, modified by:
  a) replacing alanine at position 2 or position 12 with asparagine;
  b) replacing proline at position 25, position 38, position 126 or position 171 with asparagine;
  c) replacing arginine at position 35 with asparagine;
  d) replacing serine at position 37 with asparagine and proline at position 38 with any other naturally occurring amino acid;
  e) replacing serine at position 166 with asparagine;
  f) replacing leucine at position 172 with asparagine;
  g) replacing aspartic acid at position 194 with asparagine;
  h) replacing threonine at position 114 with asparagine and proline at position 115 with any naturally occurring amino acid; or
  i) replacing arginine at position 218 with asparagine.

In yet another aspect, the modified FLINT polypeptide comprises substituting charged or hydrophilic residues with salt-bridge forming residues, said polypeptide having an amino acid sequence of SEQ ID NO:1, modified by:
  a) replacing asparagine at position 63 with tryptophan;
  b) replacing glycine at position 67 with aspartic acid and replacing alanine at position 94 or glycine at position 95 with tyrosine;
  c) replacing arginine at position 69 with glutamic acid;
  d) replacing arginine at position 82 with glutamic acid or threonine;
  e) replacing alanine at position 94 with tyrosine and replacing glycine at position 95 with aspartic acid;
  f) replacing phenylalanine at position 96 with glutamine;
  g) replacing alanine at position 101 with threonine; or
  h) replacing glycine at position 95 with aspartic acid.

In yet another aspect, the modified FLINT polypeptide comprises changing charged residues to hydrophilic residues having an amino acid sequence of SEQ ID NO:1, modified by:
  a) replacing arginine at position 10 with glutamine, asparagine, serine or threonine, provided that when the replacing amino acid is asparagine, then alanine at position 12 is optionally replaced with serine or threonine;
  b) replacing glutamic acid at position 13 with glutamine, asparagine, serine or threonine, provided that when the replacing amino acid is asparagine, then glycine at position 15 is optionally replaced with serine or threonine;

c) replacing glutamic acid at position 16 with glutamine, asparagine, serine or threonine, provided that when the replacing amino acid is asparagine, then leucine at position 18 is optionally replaced with serine or threonine;

d) replacing arginine at position 17 with glutamine, asparagine, serine or threonine, provided that when the replacing amino acid is asparagine, then valine at position 19 is optionally replaced with serine or threonine;

e) replacing arginine at position 31 with glutamine, asparagine, serine or threonine, provided that when the replacing amino acid is asparagine, then cysteine at position 33 is optionally replaced with serine or threonine;

f) replacing arginine at position 34 with glutamine, asparagine, serine or threonine, provided that when the replacing amino acid is asparagine, then aspartic acid at position 36 is optionally replaced with serine or threonine;

g) replacing arginine at position 35 with glutamine, asparagine, serine or threonine;

h) replacing aspartic acid at position 36 with glutamine, asparagine, serine or threonine, provided that when the replacing amino acid is asparagine, then proline at position 38 is optionally replaced with serine or threonine;

i) replacing arginine at position 143 with glutamine, asparagine, serine or threonine, provided that when the replacing amino acid is asparagine, then cysteine at position 145 is optionally replaced with serine or threonine; or j) replacing aspartic acid at position 161 with glutamine, asparagine, serine or threonine, provided that when the replacing amino acid is aspargine, then leucine at position 163 is optionally replaced with serine or threonine.

The optional replacement with serine or threonine of the amino acid two positions removed from the replacing asparagine in the direction of the C-terminus creates new N-linked glycosylation site motifs, i.e. NXS/T. Modified FLINT polypeptides with new glycosylation site motifs are preferably prepared from recombinant mammalian host cells that express a gene encoding said polypeptide, thereby preparing an N-glycosylated product. Glycosylation site motifs are discussed in greater detail hereinbelow.

In yet another embodiment, the present invention is a modified FLINT polypeptide or fragment thereof, said polypeptide comprising the amino acid sequence of SEQ ID NO:1 modified by:

a) replacing alanine at position 2, 12, 107, 179 or 209 with threonine;

b) replacing threonine at position 4 or 162 with alanine;

c) replacing valine at position 1 or isoleucine at position 110 with methionine;

d) replacing glutamic acid at position 13 with aspartic acid;

e) replacing arganine at position 17 with tryptophan;

f) replacing alanine at position 75 with proline;

g) replacing serine at position 102 with leucine;

h) replacing glycine at position 169 with alanine;

i) replacing glutamic acid at position 183 with lysine;

j) replacing glutamine at position 225 with arginine;

k) replacing glycine at position 237 with glutamic acid; or l) replacing valine at position 270 with glycine; and physiologically acceptable salts thereof.

In yet another aspect, the modified FLINT polypeptide comprises new glycosylation sites having an amino acid sequence of SEQ ID NO:1, modified by:

a) replacing alanine at position 12 with asparagine and optionally replacing glutamic acid at position 13 with glutamine;

b) replacing arginine at position 34 with asparagine and replacing aspartic acid at position 36 with threonine;

c) replacing arginine at position 35 with asparagine and optionally replacing serine at position 37 with threonine;

d) replacing serine at position 132 with asparagine and optionally replacing serine at position 134 with threonine;

e) replacing aspartic acid at position 194 with asparagine and optionally replacing serine at position 196 with threonine;

f) replacing arginine at position 35 and aspartic acid at position 194 with asparagine;

g) replacing alanine at position 12 with asparagine, optionally replacing glutamic acid at position 13 with glutamine, replacing aspartic acid at position 194 with asparagine and optionally replacing serine at position 196 with threonine;

h) replacing arginine at position 34 with asparagine, replacing aspartic acid at position 36 with threonine, replacing aspartic acid at position 194 with asparagine and optionally replacing serine at position 196 with threonine;

i) replacing arginine at position 35 and aspartic acid at position 194 with asparagine and replacing serine at position 37 and/or position 196 with threonine; or j) replacing arginine at position 218 with glutamine.

k) replacing glycine at position 26 with aspartic acid and replacing serine at position 132 with asparagine; or l) replacing alanine at position 12 with asparagine, replacing serine at position 132 with asparagine, and replacing serine at position 134 with threonine.

The present invention includes FLINT polypeptide fragments and modified fragments that are biologically active, in vivo or in vitro. Examples of preferred fragments include a polypeptide consisting of amino acids 1 through 218 of SEQ ID NO:1, as well modified versions thereof, as described above. Also included are physiologically acceptable salts of the modified FLINT polypeptides and the fragments thereof.

The present invention also includes the polypeptides and fragments described above, modified so that glycine at the position corresponding to 214 of SEQ ID NO: 1 is replaced with alanine.

Another embodiment of the present invention is a peptide derivative (hereinafter the "FLINT peptide derivative") comprising a modified FLINT polypeptide, FLINT fragment, or a modified FLINT polypeptide fragment.

Another embodiment of the present invention is a pharmaceutical formulation comprising the FLINT peptide derivative, the FLINT polypeptide or the FLINT polypeptide fragment, or modified versions thereof, and a suitable pharmaceutical carrier.

Another embodiment of the present invention relates to a method of inhibiting binding of FAS Ligand to FAS or LIGHT to LTβR and/or TR2/HVEM in a subject in need of such inhibition. The method comprises administering to the subject an effective amount of a FLINT derivative effective for inhibiting said binding.

Another embodiment of the present invention is a method of treating a subject with runaway apoptosis. The method comprises administering to the subject an effective amount of a FLINT peptide derivative.

Another embodiment of the present invention is a fusion protein represented by Structural Formula (I):

(I)

Fc is the Fc Fragment of an antibody or an analog thereof, preferably a human antibody and more preferably IgG, IgG1, IgG2 or IgG4. Preferably, Fc is an analog of the Fc Fragment in which from about five to about fifteen amino acids have been truncated from the N-terminus of both heavy chains of an Fc Fragment.

Each X is independently a modified FLINT polypeptide, a modified FLINT polypeptide fragment, FLINT fragment, or FLINT peptide derivative. Preferably, each X is the same.

Each modified FLINT polypeptide, a modified FLINT polypeptide fragment, FLINT fragment, or FLINT peptide derivative represented by X is covalently linked at its C-terminus to the N-terminus of one of the heavy chains which form the Fc Fragment of the antibody.

Yet another embodiment relates to a nucleic acid that encodes a FLINT peptide derivative of the present invention, for example, a fragment comprising residues 1 through 218 of SEQ ID NO:1.

Yet another embodiment of the present invention is a polydeoxynucleotide encoding a FLINT peptide derivative, a modified FLINT polypeptide, a modified FLINT polypeptide fragment, FLINT fragment, or a fusion protein represented by Structural Formula (I).

Yet another embodiment of the present invention is a polydeoxynucloetide derivative. The polydeoxynucleotide derivative comprises one of the polydexoynucleotides of the present invention, described above.

Yet another embodiment of the present invention is a vector comprising a polydeoxynucleotide encoding encoding a FLINT peptide derivative, a modified FLINT polypeptide, a modified FLINT polypeptide fragment or a fusion protein represented by Structural Formula (I).

Yet another embodiment of the present invention is a host cell comprising the vector described in the previous paragraph.

Yet another embodiment of the present invention relates to methods of producing a modified FLINT polypeptide, a modified FLINT polypeptide fragment, FLINT fragment, or a FLINT peptide derivative. For example, a method comprising the step of culturing the host cell described in the previous paragraph under conditions suitable for expressing the polydeoxynucleotide encoding a FLINT peptide derivative, a modified FLINT polypeptide or a modified FLINT polypeptide fragment, FLINT fragment, and isolating the resulting protein.

Another embodiment of the invention relates to the use of a FLINT derivative in treating and/or inhibiting a disease including acute lung injury (ALI), acute respiratory distress syndrome (ARDS), pulmonary fibrosis (PF), and chronic obstructive pulmonary disease (COPD).

Further aspects of the invention include formulations, having a FLINT analog or Fc-FLINT derivative fusion protein as an active ingredient said formulations adapted for treating and/or inhibiting ALI, ARDS, COPD, and PF and other disease treatable by FLINT.

Yet other embodiments of the invention include the use of FLINT analog in the preparation of medicaments useful in treating and/or inhibiting ALI, ARDS, COPD, and PF.

The invention also relates to a method for treating and/or inhibiting ischemia injury during organ transplantation comprising the use of a FLINT analog.

The present invention encompasses a method for inhibiting and/or treating an individual suffering from ALI, comprising administration of a therapeutically amount of FLINT analog to said individual. The invention also relates to a method of treating or inhibiting ARDS in an individual, comprising administration of a therapeutically amount of FLINT analog to said individual. Additionally, the invention includes a method of treating or inhibiting COPD in an individual comprising administration of a therapeutically effective amount of FLINT analog to said individual. Additionally, the invention includes a method of treating or inhibiting pulmonary fibrosis in an individual comprising administration of a therapeutically amount of FLINT analog to said individual.

In another embodiment, the present invention relates to the use of FLINT analog to inhibit T lymphocyte activation.

DETAILED DESCRIPTION OF THE INVENTION

As used herein the term "FLINT analog" or "analog" refers to FLINT polypeptide derivatives, including modified FLINT polypeptides, modified FLINT polypeptide fragments, and FLINT fragments.

The term "FLINT peptide derivative" or "FLINT derivative" refers to, or comprises, a modified FLINT polypeptide, FLINT fragment, or a modified FLINT polypeptide fragment.

The term "modified FLINT polypeptide" refers to a polypeptide having the amino acid sequence of FLINT modified at one or more positions by amino acid substitutions, deletions, and/or additions.

The term "modified FLINT fragment" refers to a fragment of FLINT that retains biological activity, e.g. the ability to bind FasL or the ability to bind LIGHT. A preferred fragment comprises amino acid residues 1 to 218 of SEQ ID NO:1.

As used herein the term "FLINT" refers to both native FLINT (SEQ ID NO:3) and mature FLINT (SEQ ID NO:1).

SEQ ID NO:1—Mature human FLINT, i.e. native FLINT minus the leader sequence.

SEQ ID NO:2—Nucleic acid/cDNA encoding mature human FLINT.

SEQ ID NO:3—Native human FLINT.

SEQ ID NO:4—Human FLINT leader sequence.

BRIEF DESCRIPTION OF THE DRAWINGS

FIG. 1. Activity of wild-type FLINT and R218Q FLINT-Fc in Jurket cell apoptosis assay.

FIG. 2. 48h survival rates of Balb/c mice given LPS it induce septic shock and treated with FLINT or R218QFc.

One embodiment of the present invention relates to fragments and modified fragments of FLINT that preferably retain biological activity. Biological activity may relate to in vitro and/or in vivo effects, e.g. the ability of a FLINT analog to bind FasL and/or the ability to bind LIGHT. Alternatively, FLINT biological activity may relate to the ability of a FLINT analog, or fragment thereof, or modified fragment thereof, to treat or prevent a disease or condition in a mammal, including a human, when administered in an effective amount to a mammal in need thereof. Fragments may comprise defined sub-regions of the FLINT molecule. For example, sub-region D1 relates to amino acid residues 1 through 42 of SEQ ID NO:1; sub-region D2 relates to residues 43 through 85 of SEQ ID NO:1; sub-region D3 relates to residues 86 through 122 of SEQ ID NO:1; and D4 relates to residues extending from residue 123 through 165 of SEQ ID NO:1. Functional FLINT fragments comprise one or more of the domains D1–D4. Preferably a FLINT fragment comprises domains D1–D4; alternatively, comprising domains D2 and D3; alternatively comprising domains D2–D4; alternatively comprising domains D3 and D4; and alternatively comprising domain D4.

A preferred FLINT polypeptide fragment consists of amino acid residues 1 through 218 of SEQ ID NO:1, referred to herein as "FLINT metabolite;" alternatively to residues 1 through 216 of SEQ ID NO:1. Said FLINT fragments and preferred FLINT fragments may comprise a leader sequence, for example SEQ ID NO:4.

FLINT metabolite and other FLINT fragments bind FasL and LIGHT. LIGHT, a new member of the TNF family, is a membrane-bound ligand that triggers distinct biological responses. LIGHT may play a role in immune modulation, and it appears to be involved in herpes virus entry (see Zhai et al., J. Clin. Invest. 102, 1142–1151, 1998; Montgomery et al. Cell, 87, 427–436, 1996). Soluble LIGHT inhibits the proliferation of various tumor cells and appears to bind the receptors LTβR and TR2 (also referred to as herpes virus entry mediator, HVEM). LIGHT is expressed highly in activated lymphocytes and evokes immune modulation from hematopoietic cells. For example, LIGHT stimulates the secretion of IFNγ. LIGHT also induces apoptosis of tumor cells that express the LTβR and TR2/HVEM receptors. The cytotoxic effect of LIGHT is enhanced by IFNγ, which can be blocked by addition of soluble LTβR-Fc or TR2/HVEM-Fc. LIGHT is produced primarily by activated T lymphocytes. When LIGHT binds to HVEM on the surface of T cells it stimulates T cell proliferation (J. A. Harrop et al. J. Biol. Chem. 273, 27548–27556, 1998).

The present invention relates further to the use of FLINT analog and/or FLINT metabolite or other FLINT fragment to bind LIGHT, thereby inhibiting T cell activation. T cell activation can be chronically suppressed when advantageous, for example, following organ transplantation to prevent rejection, in the treatment of autoimmune diseases, and in treating systemic inflammatory responses.

FLINT fragments such as FLINT metabolite including modified derivatives thereof are useful in binding LIGHT and modulating the effects of LIGHT on immune response and apoptosis. Therefore, in another embodiment a FLINT analog including FLINT metabolite or a modified version thereof, is used to bind LIGHT thereby inhibiting apoptosis and/or immune modulation.

The FLINT fragments of the invention can be produced in vivo or in vitro by recombinant techniques or by direct chemical synthesis. FLINT metabolite is produced in vivo when administered exogenously to a mammal. FLINT fragments may be generated by any number of suitable techniques, including chemical synthesis of any portion of SEQ ID NO:1, or SEQ ID NO:3, proteolytic digestion of FLINT, or by recombinant DNA mutagenesis techniques, well known to the skilled artisan. See. e.g. K. Struhl, "Reverse biochemistry: Methods and applications for synthesizing yeast proteins in vitro," Meth. Enzymol. 194, 520–535. In a preferred recombinant method, a nested set of deletion mutations are introduced into a gene or cDNA (e.g. SEQ ID NO:2) encoding FLINT such that varying amounts of the coding region are deleted, either from the amino terminal end, or from the carboxyl end of the protein molecule. This method can also be used to create internal fragments of FLINT in which both the carboxyl and amino terminal ends are removed. Several appropriate nucleases can be used to create such deletions, for example Bal31, or in the case of a single stranded nucleic acid molecule, mung bean nuclease. For simplicity, it is preferred that a FLINT-encoding nucleic acid be cloned into a single-stranded cloning vector, such as bacteriophage M13, or equivalent. If desired, the resulting deletion fragments can be subcloned into any suitable vector for propagation and expression in any suitable host cell.

In a preferred embodiment for in vitro production of FLINT metabolite, FLINT is treated with a serine protease, for example, thrombin or trypsin, to cleave between the Arg residue at position 218 and the Ala residue at position 219 of SEQ ID NO:1.

Production of FLINT Metabolite and Protease-resistant Analogs

FLINT undergoes proteolysis in vivo to produce at least two major peptide fragments. One of the fragments consists of residues 1 through 218 of SEQ ID NO:1 (alternatively residues 1 through 247 of SEQ ID NO:3), termed herein "FLINT metabolite;" the other consists of residues 219 through 271 of SEQ ID NO:1 (alternatively residues 248 through 300 of SEQ ID NO:3). Cleavage at the 218 position in vitro can be achieved when native FLINT (SEQ ID NO:3), or mature FLINT (SEQ ID NO:1), is treated with a trypsin-like enzyme, for example, thrombin, trypsin or other serine protease. Thus it is likely that a serine protease is responsible for the in vivo proteolysis of FLINT.

The term "negatively charged group" or "negatively charged amino acid" refers to Asp or Glu.

The term "positively charge group" or "positively charged amino acid" refers to His, Arg, or Lys.

The term "polar uncharged" or "polar uncharged amino acid" refers to Cys, Thr, Ser, Gly, Asn, Gln, and Tyr.

The term "nonpolar" or "nonpolar amino acid" refers to Ala, Pro, Met, Leu, Ile, Val, Phe, or Trp.

The term "naturally-occurring amino acid" refers to any of the 20 L-amino acids that are found in proteins.

The term "native FLINT" refers to SEQ ID NO:3.

The term "mature FLINT" refers to SEQ ID NO:1.

The term "FLINT" refers to native and mature FLINT from human, other primates, and other mammalian and non-mammalian sources.

As used herein "half-life" refers to the time required for approximately half of FLINT or a FLINT analog to be proteolytically cleaved between positions 218 and 219 of SEQ ID NO:1, in vitro and/or in vivo, as determined by any suitable means. The term is used as a measure of exposure to full-length FLINT or FLINT analog (i.e. not proteolytically cleaved).

The term "protease-resistant" or "resistant" refers to a FLINT analog that, when compared with FLINT, or FLINT fragment, is more resistant to proteolysis between residues 218 and 219 of SEQ ID NO:1. Protease resistant analogs differ from FLINT by one or more amino acid substitutions, deletions, inversions, additions, and/or changes in glycosylation sites, or patterns, as compared with or against native FLINT, or mature FLINT, or other FLINT fragment. Preferably these changes occur in the region from about position 214 through position 222 of SEQ ID NO:1.

The term "protease-resistant" contemplates degrees of resistance to proteolysis at position 218 from complete resistance to partial resistance. Thus, a "substantially resistant" analog shows a degree of resistance to proteolysis at position 218, for example, an analog with a half-life that is at least about 25% greater than native FLINT when treated or exposed to a suitable protease. Preferably a substantially resistant FLINT analog possesses a half-life resistance that is at least about 2-fold greater than native FLINT.

Susceptibility to proteolysis will depend on such factors as the amino acid sequence at or near the recognition site of the particular proteolytic enzyme involved, and on the physical and chemical environment in which a sample protein is located. Factors such as these can affect the $K_M$ and/or rate of proteolysis by a proteolytic enzyme. A sequence that is recognized by thrombin is LVPR/. Other sequences are also recognized by thrombin, e.g. VDPR/and others. The charge density and steric properties operative at the enzymes active site will determine the degree to which proteolysis occurs. All such embodiments are intended to be within the scope of the invention.

Protease resistance, as contemplated herein, refers to the sensitivity of a FLINT analog to proteolysis at position 218, in vivo or in vitro. For example, the resistance of an analog to a trypsin-like protease such as thrombin or trypsin, or other serine protease is compared with the resistance shown by FLINT under the same conditions. It is preferred that a FLINT analog display a half-life at least 5% greater than FLINT, alternatively at least 10%, 20%, 30%, 40%, or between 50% to 100% greater than wild type FLINT, as determined by the relative quantity of full length molecules to smaller digestion products (e.g. fragments 1–218 and 219–271 of SEQ ID NO:1). Any suitable method for making a qualitative and/or quantitative assessment of said relative quantities can be used, for example, polyacrylamide gel electrophoresis. Most preferably, a resistant analog possesses a half-life that is from about 1-fold to 2-fold greater than FLINT to about 100-fold or greater than FLINT. Applicants have discovered that FLINT polypeptides are cleaved in vivo between the arginine residue at position 218 and the alanine residue at position 219 of SEQ ID NO:1, probably by a trypsin-like protease. A cleavage product of this reaction comprises residues 1–218 of SEQ ID NO:1, termed "FLINT metabolite." FLINT metabolite can be produced in vitro by treating a FLINT polypeptide with a trypsin-like protease, for example, thrombin, trypsin, or other serine protease.

One embodiment of the present invention relates to a method to produce analogs of a FLINT polypeptide that are resistant to proteolysis between positions 218 and 219 of SEQ ID NO:1 and retain biological activity. Biological activity relates to the capacity of an analog to bind FasL and/or LIGHT, and may include an inhibition of apoptosis in vivo and/or in vitro.

Another embodiment of the present invention relates to analogs of a FLINT polypeptide that are resistant to proteolysis between positions 218 and 219 of SEQ ID NO:1 and retain biological activity. Biological activity relates to the capacity of an analog to bind FasL and/or LIGHT, and may include an inhibition of apoptosis in vivo and/or in vitro.

Preferred FLINT analogs provide a half-life at least 5%, 10%, 20%, 30%, 40%, or between 50% to 100% greater than FLINT, as determined by the ratio over time of full length FLINT to digestion products comprising FLINT metabolite and the carboxyl fragment (i.e. residues 219–271 of SEQ ID NO1); most preferably a FLINT analog possesses a half-life at least 2-fold to 100-fold or greater than FLINT.

FLINT analogs comprise one or more primary or secondary structural changes, for example amino acid substitutions, deletions, inversions, additions, or changes in glycosylation sites or patterns and/or combinations thereof that prevent or diminish proteolysis, and/or the rate thereof, between positions 218 and 219 of SEQ ID NO:1. Preferably these changes occur at or near the thrombin-like recognition sequence, in the case of FLINT, PTPR; most preferably, at or near the PR dipeptide sequence at positions 217 and 218 of SEQ ID NO:1. As the skilled artisan understands, residues at or near a recognition site can also affect the susceptibility of the substrate protein to proteolysis by altering the charge milieu at the active site and/or by creating alterations by steric hindrance in the region of the active site.

Therefore, the invention contemplates FLINT analogs comprising amino acid changes in FLINT, preferably in the region from about position 214 through position 222 of SEQ ID NO:1 or the comparable region of SEQ ID NO:3, wherein said analogs are resistant to proteolysis at position 218 of SEQ ID NO:1.

Also contemplated are protease-resistant FLINT analogs comprising substitutions, deletions, insertions, inversions, additions, or changes in glycosylation sites or patterns that occur outside the preferred window comprising residues 214 through 222 of SEQ ID NO:1. As the skilled artisan understands, many substitutions, and/or other changes in a protein's sequence or structure, can be made without substantially affecting the biological activity of the protein. For example, making conservative amino acid substitutions, or, changing one amino acid for another from the same class of amino acids, for example negatively charged residues, positively charged residues, polar uncharged residues, and non-polar residues, or any other classification acceptable in the art are often without effect on function. Such changes are intended to be within the scope of the present invention.

In one embodiment, a single amino acid change is made within this region; alternatively, at least two changes are made within this region; alternatively, at least three changes are made within this region; alternatively, at least four changes are made within this region.

In one embodiment, the invention relates to FLINT analog polypeptides and nucleic acids that are defined with reference to a percent identity similarity to SEQ ID NO:1, SEQ ID NO:2, and/or SEQ ID NO:3. Sequence identity refers to a comparison between two molecules using standard algorithms well known in the art. Although any suitable sequence comparison algorithm can be used for this purpose, for illustration, this embodiment shall be described with reference to the well-known Smith-Waterman algorithm using SEQ ID NO:1 as the reference sequence to define percent identity to a comparator sequence. When sequence identity is used with reference to a polypeptide, the entire polypeptide may be used in the comparison or a defined sub-region thereof.

The choice of parameter values for matches, mismatches, and inserts or deletions is arbitrary. A preferred set of values for use with the Smith-Waterman algorithm is set forth in the "maximum similarity segments" approach, which uses values of 1 for a matched residue, and $-\frac{1}{3}$ for a mismatched residue (See Waterman, *Bulletin of Mathematical Biology*, 46, 473–500, 1984). Insertions and deletions (indels), x, are weighted as follows:

$$X_k = 1 + k/3$$

Where k is the number of residues in a given insert or deletion.

For example, a comparator sequence that has 20 substitutions and 3 insertions relative to the 250 residue reference protein sequence would have an identity of:

$$[(1\times250)-(\tfrac{1}{5}\times20)-(1+3/3)]/250=96\%$$

identical.

FLINT protease-resistant analogs of the present invention can easily be tested for biological activity and/or sensitivity to proteolysis as described herein. Biological activity can be assessed using either in vitro (see Examples 5 & 8) or in vivo (see Example 11) models as described herein.

In another embodiment, the invention relates to a FLINT analog comprising one or more amino acid substitution(s) in the region 214–222 of SEQ ID NO:1, and/or amino acids 243–251 of SEQ ID NO:3.

In another embodiment, the invention relates to a FLINT analog comprising an amino acid substitution(s) in the region comprising amino acids 214–222 of SEQ ID NO:1, selected from the group consisting of:
- a. Gly at position 214 is replaced by any naturally occurring amino acid other than Gly;
- b. Pro at position 215 is replaced by any naturally occurring amino acid other than Pro;
- c. Thr at position 216 is replaced by any naturally occurring amino acid other than Thr;
- d. Pro at position 217 is replaced by any naturally occurring amino acid other than Pro;
- e. Arg at position 218 is replaced by any naturally occurring amino acid other than Arg;
- f. Ala at position 219 is replaced by any naturally occurring amino acid other than Ala;
- g. Gly at position 220 is replaced by any naturally occurring amino acid other than Gly;
- h. Arg at position 221 is replaced by any naturally occurring amino acid other than Arg;
- i. Ala at position 222 is replaced by any naturally occurring amino acid other than Ala.

In another embodiment, the invention relates to a FLINT analog comprising an amino acid substitution in the region comprising amino acids 214–222 of SEQ ID NO:1, selected from the group consisting of:
- a. Gly at position 214 is replaced by a positively charged amino acid that is not Gly;
- b. Pro at position 215 is replaced by a positively charged amino acid that is not Pro;
- c. Thr at position 216 is replaced by a positively charged amino acid that is not Thr;
- d. Pro at position 217 is replaced by a positively charged amino acid that is not Pro;
- e. Arg at position 218 is replaced by a positively charged amino acid that is not Arg;
- f. Ala at position 219 is replaced by a positively charged amino acid that is not Ala;
- g. Gly at position 220 is replaced by a positively charged amino acid that is not Gly;
- h. Arg at position 221 is replaced by a positively charged amino acid that is not Arg;
- i. Ala at position 222 is replaced by a positively charged amino acid that is not Ala.

In another embodiment, the invention relates to a FLINT analog comprising an amino acid substitution in the region comprising amino acids 214–222 of SEQ ID NO:1, selected from the group consisting of:
- a. Gly at position 214 is replaced by a negatively charged amino acid that is not Gly;
- b. Pro at position 215 is replaced by a negatively charged amino acid that is not Pro;
- c. Thr at position 216 is replaced by a negatively charged amino acid that is not Thr;
- d. Pro at position 217 is replaced by a negatively charged amino acid that is not Pro;
- e. Arg at position 218 is replaced by a negatively charged amino acid that is not Arg;
- f. Ala at position 219 is replaced by a negatively charged amino acid that is not Ala;
- g. Gly at position 220 is replaced by a negatively charged amino acid that is not Gly;
- h. Arg at position 221 is replaced by a negatively charged amino acid that is not Arg;
- i. Ala at position 222 is replaced by a negatively charged amino acid that is not Ala.

In another embodiment, the invention relates to a FLINT analog comprising an amino acid substitution in the region comprising amino acids 214–222 of SEQ ID NO:1, selected from the group consisting of:
- a. Gly at position 214 is replaced by a polar uncharged amino acid that is not Gly;
- b. Pro at position 215 is replaced by a polar uncharged amino acid that is not Pro;
- c. Thr at position 216 is replaced by a polar uncharged amino acid that is not Thr;
- d. Pro at position 217 is replaced by a polar uncharged amino acid that is not Pro;
- e. Arg at position 218 is replaced by a polar uncharged amino acid that is not Arg;
- f. Ala at position 219 is replaced by a polar uncharged amino acid that is not Ala;
- g. Gly at position 220 is replaced by a polar uncharged amino acid that is not Gly;
- h. Arg at position 221 is replaced by a polar uncharged amino acid that is not Arg;
- i. Ala at position 222 is replaced by a polar uncharged amino acid that is not Ala.

In another embodiment, the invention relates to a FLINT analog comprising an amino acid substitution in the region comprising amino acids 214–222 of SEQ ID NO:1, selected from the group consisting of:
- a. Gly at position 214 is replaced by a nonpolar amino acid that is not Gly;
- b. Pro at position 215 is replaced by a nonpolar amino acid that is not Pro;
- c. Thr at position 216 is replaced by a nonpolar amino acid that is not Thr;
- d. Pro at position 217 is replaced by a nonpolar amino acid that is not Pro;
- e. Arg at position 218 is replaced by a nonpolar amino acid that is not Arg;
- f. Ala at position 219 is replaced by a nonpolar amino acid that is not Ala;
- g. Gly at position 220 is replaced by a nonpolar amino acid that is not Gly;
- h. Arg at position 221 is replaced by a nonpolar amino acid that is not Arg;
- i. Ala at position 222 is replaced by a nonpolar amino acid that is not Ala.

In another embodiment, the invention relates to a FLINT analog comprising an amino acid substitution in the region comprising amino acids 214–222 of SEQ ID NO:1, selected from the group consisting of:
 a. Arg at position 218 is replaced by Gln;
 b. Arg at position 218 is replaced by Glu;
 c. Thr at position 216 is replaced by Pro;
 d. Arg at position 218 is replaced by Ala;
 e. Arg at position 218 is replaced by Gly;
 f. Arg at position 218 is replaced by Ser;
 g. Arg at position 218 is replaced by Val
 h. Arg at position 218 is replaced by Tyr;
 i. Pro at position 217 is replaced by Tyr
 j. Thr at position 216 is replaced by Pro, and Arg at position 218 is replaced by Gln.

In another embodiment, the present invention relates to a FLINT analog comprising SEQ ID NO:1 wherein Arg at position 34 is replaced by Asn, Asp at position 36 is replaced by Thr, and Arg at position 218 is replaced by Gln, Glu, Ala, Gly, Ser, Val, or Tyr. In another embodiment, the present invention relates to a FLINT analog comprising SEQ ID NO:1 wherein Arg at position 34 is replaced by Asn, Asp at position 36 is replaced by Thr, Asp at position 194 is replaced by Asn, Ser at position 196 is replaced by Thr, and Arg at position 218 is replaced by Gln, Glu, Ala, Gly, Ser, Val, or Tyr.

In another embodiment, the present invention relates to a FLINT analog comprising one or more amino acid substitution(s) within SEQ ID NO:1 wherein Arg at position 34 is replaced by Asn, Asp at position 36 is replaced by Thr, and Arg at position 218 is replaced by an amino acid selected from the group consisting of:
 a. any naturally occurring amino acid that is not Arg;
 b. any positively charged amino acid that is not Arg;
 c. any negatively charged amino acid that is not Arg;
 d. any polar uncharged amino acid that is not Arg;
 e. any nonpolar amino acid that is not Arg; and
 f. an amino acid that is Glu, Gln, Ala, Gly, Ser, Val, or Tyr.

In another embodiment, the present invention relates to a FLINT analog comprising one or more amino acid substitution(s) within SEQ ID NO:1 wherein Arg at position 34 is replaced by Asn, Asp at position 36 is replaced by Thr, Asp at position 194 is replaced by Asn, Ser at position 196 is replaced by Thr, and Arg at position 218 is replaced by an amino acid selected from the group consisting of:
 a. any naturally occurring amino acid that is not Arg;
 b. any positively charged amino acid that is not Arg;
 c. any negatively charged amino acid that is not Arg;
 d. any polar uncharged amino acid that is not Arg;
 e. any nonpolar amino acid that is not Arg; and
 f. an amino acid that is Glu, Gln, Ala, Gly, Ser, Val, or Tyr.

In another embodiment, the present invention relates to a FLINT analog comprising one or more amino acid substitution(s) within SEQ ID NO:1 wherein Ser at position 132 is replaced by Asn, and Arg at position 218 is replaced by an amino acid selected from the group consisting of:
 a. any naturally occurring amino acid that is not Arg;
 b. any positively charged amino acid that is not Arg;
 c. any negatively charged amino acid that is not Arg;
 d. any polar uncharged amino acid that is not Arg;
 e. any nonpolar amino acid that is not Arg; and
 an amino acid that is Glu, Gln, Ala, Gly, Ser, Val, or Tyr.

A FLINT peptide derivative comprises a modified FLINT polypeptide or a modified FLINT polypeptide fragment, or FLINT fragment, and one or more other moieties. Examples of FLINT peptide derivatives are provided hereinbelow.

One example of a FLINT peptide derivative is a modified FLINT polypeptide or a fragment thereof with an oligopeptide or amino acid added onto the N-terminus and/or C-terminus. An "oligopeptide" is a chain of from two to about twenty amino acids connected at their N- and C-termini by peptide bonds. Suitable oligopeptides and amino acids are those which do not significantly decrease the binding of FLINT to FAS ligand, do not substantially detract from the pharmaceutical and pharmacological properties of FLINT and do not significantly decrease the in vivo half-live of FLINT. Examples include leader sequences found in native FLINT, such as MRALEGPGLS LLCLVI-ALPA LLPVPAVRG (SEQ ID NO.: 4).

FLINT peptide derivatives also include modified and unmodified FLINT peptides and fragments thereof, with one or more polyethylene glycol groups (hereinafter "PEG" groups). The PEG groups can be bonded to the N-terminus or to amine groups or thiol groups in the amino acid side chain(s) of modified FLINT polypeptides or fragments thereof. Suitable PEG groups generally have a molecular weight between about 5000 and 20,000 atomic mass units. Procedures for preparing PEGylated polypeptides are disclosed in Mumtaz and Bachhawat, *Indian Journal of Biochemistry and Biophysics* 28:346 (1991) and Franciset al., *International Journal of Hematology* 68:1 (1998), the entire teachings of which are incorporated herein by reference.

Yet another example of a FLINT peptide derivatives is a molecule comprising two or more modified or unmodified FLINT polypeptides or two or more fragments thereof, e.g., a dimerized modified FLINT polypeptide or a dimerized modified FLINT polypeptide fragment. Dimerization can be accomplished, for example, by means of a PEG polymer chain as described in Espat et al., Journal of Surgical Research 59: 153 (1995) or through a C-terminal fusion with another dimerization inducing domain such as a leucine zipper as described in O'Shea et al., *Science* 254:539 (1991). The entire teachings of Espat and O'Shea are incorporated herein by reference. In another example, an amino acid residue in the protein is replaced with a cysteine followed by formation of an intermolecular disulfide bond to form a modified FLINT polypeptide dimer, a dimer of a modified FLINT polypetide or a dimer of a FLINT peptide derivative. A dimerized polypeptide can be formed, for example, by replacing serine 116 or glutamine 122 of a modified FLINT polypeptide with cysteine, followed by intermolecular disulfide bond formation.

In yet another example, the FLINT peptide derivative is a fusion protein comprising a modified FLINT polypeptide or fragment thereof fused to another protein or glycosylated domain of another protein. "Fusion protein" denotes a hybrid protein molecule not found in nature comprising a translational fusion or enzymatic fusion in which two or more different proteins or fragments thereof are covalently linked on a single polypeptide chain. Human serum albumin and the C-terminal domain of thrombopoietin are examples of proteins which could be fused with modified FLINT or modified FLINT fragments. Procedures for preparing fusion proteins are disclosed in EP394,827, Tranecker et al., *Nature* 331:84 (1988) and Fares, et al., *Proc. Natl. Acad. Sci. USA* 89:4304 (1192), the entire teachings of which are incorporated herein by reference.

As used herein, "Fc Fragment" of an antibody has the meaning commonly given to the term in the field of immunology. Specifically, this term refers to an antibody fragment which binds complement and is obtained by removing the two antigen binding regions (the Fab Fragments) from the antibody. Thus, the Fc Fragment is formed from approximately equal sized fragments from both heavy chains, which associate through non-covalent interactions and disulfide bonds. The Fc Fragment includes the hinge regions and extends through the $C_H2$ and $C_H3$ domains to the C-terminus of the antibody.

The modified FLINT polypeptides, the modified FLINT polypeptide fragments and the FLINT peptide derivatives of the present invention can be glycosylated or unglycosylated. A glycosylated polypeptide is modified with one or more monosaccharides or oligosaccharides. A monosaccharide is a chiral polyhydroxyalkanol or polyhydroxyalkanone which typically exists in hemiacetal form. An "oligosaccharide" is a polymer of from about 2 to about 10 monosaccharides which are generally linked by acetal bonds. One type of glycosyl group commonly found in glycosylated proteins is N-acetylneuraminic acid. A glycosylated polypeptide can be N-glycosylated and/or O-glycosylated, preferably N-glycosylated.

The term "inhibit" or "inhibiting" includes the generally accepted meaning, which includes prohibiting, preventing, restraining, slowing, stopping, or reversing progression or severity of a disease or condition.

The term "N-glycosyled polypeptide" refers to polypeptides having one or more NXS/T motifs in which the nitrogen atom in the side chain amide of the asparagine is covalently bonded to a glycosyl group. "X" refers to any naturally occurring amino acid residue except proline. The "naturally occurring amino acids" are glycine, alanine, valine, leucine, isoleucine, proline, serine, threonine, cysteine, methionine, lysine, arganine, glutamic acid, aspartatic acid, glutamine, asparagine, phenylalanine, histidine, tyrosine and tryptophan. N-Glycosylated proteins are optionally O-glycosylation.

The term "O-glycosyled polypeptide" refers to polypeptides having one or more serines and/or threonine in which the oxygen atom in the side chain is covalently bonded to a glycosyl group. O-Glycosylated proteins are optionally N-glycosylation.

The term "treatment" or "treating" as used herein, describes the management and care of a patient for the purpose of combating a disease, condition, or disorder and includes the administration of FLINT to prevent the onset of the symptoms or complications, alleviating the symptoms or complications thereof.

The polypeptides of the present invention are preferably N-glycosylated.

Glycosylated polypeptides can be prepared recombinantly by expressing a gene encoding a polypeptide in a suitable mammalian host cell, resulting in glycosylation of side chain amides found in accessible NXT/S motifs on the polypeptide surface and of side chain alcohols of surface accessible serines and threonines. Specific procedures for recombinantly expressing genes in mammalian cells are provided hereinbelow. Other procedures for preparing glycosylated proteins are disclosed in EP 640,619 to Elliot and Burn, the entire teachings of which are incorporated herein by reference. Unglycosylated polypeptides can be prepared recombinantly by expressing a gene encoding a polypeptide in a suitable prokaryotic host cell.

Other FLINT Analogs

In another embodiment, the present invention relates to analogs of FLINT predicted to alter the properties of the molecule, for example, increase the half-life, decrease aggregation, or enhance the binding affinity for FasL. For this purpose a computer-generated model of the 3-D structure of FLINT was produced, as described in Example 14.

In one class of FLINT analogs, charged residues are substituted by hydrophilic residues. It has now been found, based on homology and computer models, that a number of charged amino acid residues are exposed on the surfaces of FLINT. Moreover, these models also show that these charged amino acid residues are distinct from the site on FLINT which binds FAS Ligand and therefore thought to contribute minimally to FLINT/FAS Ligand binding affinity. Because of the large number of charged residues on the surface of FLINT, the net charge of FLINT in solution shows a large variation as the pH of the solution changes. It is believed that replacing these charged amino acid residues on the surface of FLINT with hydrophilic residues will reduce this charge gradient and thereby result in FLINT analogs which retain biological activity while exhibiting improved pharmaceutical properties. Examples of improved pharmaceutical properties include decreased aggregation, decreased absorption onto surfaces, increased solubility and improved ease of formulation.

In another embodiment, it has now been found, based on homology and computer models, that a number of hydrophobic amino acid residues are exposed of the surfaces of FLINT. These models show that hydrophobic amino acid residues are distinct from the site on FLINT which binds FAS Ligand and therefore contribute minimally to FLINT/FAS Ligand binding affinity. It is believed that biologically active FLINT analogs with improved pharmaceutical properties can be obtained by replacing these hydrophobic amino acid residues with uncharged, hydrophilic residues. Examples of improved pharmaceutical properties include decreased aggregation, decreased absorption onto surfaces, increased solubility and improved ease of formulation.

In another embodiment, it has now been found, based on computational and homology studies, that certain amino acid residues in FLINT interact with specific charged or hydrophilic amino acid residues in FAS Ligand. It is believed that FLINT analogs with improved binding affinity, and, consequently, greater potency, can be obtained by replacing these amino acids in FLINT with amino acids which can form a salt bridge or hydrogen bond with these specific charged or hydrophilic amino acid residues in FAS Ligand. The computational and homology studies also show that exposure of these newly created and already existing salt bridges or hydrogen bonds to solvent can be blocked if certain other amino acid residues in FLINT are replaced with amino acid residues having sterically hindered side chains. Blocking the exposure of these salt bridges or hydrogen bonds to solvent can further increase the affinity of these FLINT analogs for FAS Ligand.

The present invention also relates to a polydeoxynucleotide encoding a FLINT peptide derivative or a modified FLINT polypeptide, modified FLINT polypeptide fragment, or FLINT fragment. Also included in the present invention are fragments of the polydeoxynucleotide encoding a FLINT peptide derivative or a modified FLINT polypeptide.

As used herein with respect to nucleic acids, the invention is intended to cover degenerate versions that encode the same amino acid or sequence of amino acids, to account for the degeneracy of the genetic code. The skilled artisan will immediately understand that, for example, a codon for aspartic acid can be either GAT(or U for RNA) or GAC.

The invention is also intended to cover sequences that a closely related to those disclosed herein and that encode proteins with similar or the same biological activity. For example, the invention relates to sequences that are defined with reference to a percent identity similarity to SEQ ID NO;1, SEQ ID NO:2, and/or SEQ ID NO:3. Sequence identity between two molecules can be determined using any standard algorithm well known in the art. For purposes of illustration, consider the well-known Smith-Waterman algorithm as applied to compare SEQ ID NO:1 with a comparator sequence. When sequence identity is used with reference to a polypeptide, the entire polypeptide may be used in the comparison or a defined sub-region thereof.

The choice of parameters for ascertaining matches, mismatches, inserts, or deletions is arbitrary. A preferred set of values for use with the Smith-Waterman algorithm is set forth in the "maximum similarity segments" approach, which uses values of 1 for a matched residue, and $-\frac{1}{3}$ for a mismatched residue (See Waterman, *Bulletin of Mathematical Biology*, 46, 473–500, 1984). Insertions and deletions (indels), x, are weighted as follows:

$$X_k = 1 + k/3$$

Where k is the number of residues in a given insert or deletion.

For example, a comparator sequence that has 20 substitutions and 3 insertions relative to a 250 residue reference sequence. would have an identity of:

$$[(1 \times 250) - (\frac{1}{3} \times 20) - (1 + 3/3)]/250 = 96\%$$

identical.

FLINT protease-resistant analogs of the present invention can easily be tested for biological activity and/or sensitivity to proteolysis as described herein. Biological activity can be assessed using either in vitro (see Examples 5 & 8) or in vivo (see Example 11) models as described herein.

In one preferred embodiment, the polydeoxynucleotide has the deoxynucleotide sequence of SEQ ID NO:2 with the following modifications:

a) the codon encoding tryptophan at positions 157–159 is replaced with a codon encoding aspartic acid;

b) the codon encoding threonine at positions 262–264 is replaced with a codon encoding proline;

c) replacing the codon encoding alanine at positions 319–21 with a codon encoding serine, aspartic acid, glutamic acid or threonine;

d) replacing the codon encoding isoleucine at positions 328–30 with a codon encoding threonine or glutamic acid; or e) replacing the codon encoding proline at positions 310–12 with a codon encoding serine.

In another preferred embodiment, the polydeoxynucleotide has the deoxynucleotide sequence of SEQ ID NO:2 with the following modifications;

a) replacing the codon encoding alanine at positions 4–6 or positions 34–36 with a codon encoding asparagine;

b) replacing the codon encoding proline at positions 73–75 with a codon encoding asparagine;

c) replacing the codon encoding arginine at positions 103–105 with a codon encoding asparagine;

d) replacing the codon encoding serine at positions 109–111 with a codon encoding asparagine and replacing the codon encoding proline at positions 112–114 with a codon encoding any other naturally occurring amino acid;

e) replacing the codon encoding proline at positions 112–114 with a codon encoding asparagine;

f) replacing the codon encoding proline at positions 376–378 with a codon encoding asparagine;

g) replacing the codon encoding serine at positions 496–498 with a codon encoding asparagine;

h) replacing the codon encoding proline at positions 511–513 with a codon encoding asparagine;

i) replacing the codon encoding leucine at positions 514–516 with a codon encoding asparagine;

j) replacing the codon encoding aspartic acid at positions 580–582 with a codon encoding asparagine;

k) replacing the codon encoding threonine at positions 340–342 with a codon encoding asparagine and replacing the codon encoding proline at positions 343–345 with a codon encoding any naturally occurring amino acid; or l) replacing the codon encoding arginine at positions 652–654 with a codon encoding asparagine.

In another preferred embodiment, the polydeoxynucleotide has the deoxynucleotide sequence of SEQ ID NO:2 with the following modifications:

a) replacing the codon encoding asparagine at positions 187–189 with a codon encoding tryptophan;

b) replacing the codon encoding glycine at positions 199–201 with a codon encoding aspartic acid and replacing the codon encoding alanine at positions 280–282 or glycine at positions 283–285 with a codon encoding tyrosine;

c) replacing the codon encoding arginine at positions 205–07 with a codon encoding glutamic acid;

d) replacing the codon encoding arginine at positions 244–246 with a codon encoding glutamic acid or threonine;

e) replacing the codon encoding alanine at positions 280–282 with a codon encoding tyrosine and replacing the codon encoding glycine at positions 283–285 with a codon encoding aspartic acid; or f) replacing the codon encoding phenylalanine at positions 286–288 with a codon encoding glutamine;

g) replacing the codon encoding alanine at positions 301–303 with a codon encoding threonine; or i) replacing the codon encoding glycine at positions 282–285 with a condon encoding aspartic acid.

In another preferred embodiment, the polydeoxynucleotide has the deoxynucleotide sequence of SEQ ID NO:2 with the following modifications:

a) replacing the codon encoding arginine at positions 28–30 with a codon encoding glutamine, asparagine, serine or threonine, provided that when the replacing codon encodes asparagine, then the codon encoding alanine at positions 34–36 is optionally replaced with a codon encoding serine or threonine;

b) replacing the codon encoding glutamic acid at positions 37–39 with a codon encoding glutamine, asparagine, serine or threonine, provided that when the replacing codon encodes asparagine, then the codon encoding glycine at positions 43–45 is optionally replaced with a codon encoding serine or threonine;

c) replacing the codon encoding glutamic acid at positions 46–48 with a codon encoding glutamine, asparagine, serine or threonine, provided that when the replacing codon encodes asparagine, then the codon encoding leucine at positions 52–54 is optionally replaced with a codon encoding serine or threonine;

d) replacing the codon encoding arginine at positions 49–51 with a codon encoding glutamine, asparagine, serine or threonine, provided that when the replacing codon encodes asparagine, then the codon encoding valine at positions 55–57 is optionally replaced with a codon encoding serine or threonine;

e) replacing the codon encoding arginine at positions 91–93 with a codon encoding glutamine, asparagine, serine or threonine, provided that when the replacing codon encodes asparagine, then the codon encoding cysteine at positions 97–99 is optionally replaced with a codon encoding serine or threonine;

f) replacing the codon encoding arginine at positions 100–102 with a codon encoding glutamine, asparagine, serine or threonine, provided that when the replacing codon encodes asparagine, then the codon encoding aspartic acid at positions 106–108 is optionally replaced with a codon encoding serine or threonine;

g) replacing the codon encoding arginine at positions 103–105 with a glutamine, asparagine, serine or threonine;

h) replacing the codon encoding aspartic acid at positions 106–108 with a codon encoding glutamine, asparagine, serine or threonine, provided that when the replacing codon encodes asparagine, then the codon encoding proline at positions 112–114 is optionally replaced with a codon encoding serine or threonine;

i) replacing the codon encoding arginine at positions 427–429 with a codon encoding glutamine, asparagine, serine or threonine, provided that when the replacing codon encodes asparagine, then the codon encoding cysteine at positions 433–435 is optionally replaced with a codon encoding serine or threonine; or j) replacing the codon encoding aspartic acid at positions 481–483 with a codon encoding glutamine, asparagine, serine or threonine, provided that when the replacing codon encodes aspargine, then the codon replacing leucine at positions 487–489 is optionally replaced with a codon encoding serine or threonine.

In another preferred embodiment, the polydeoxynucleotide has the deoxynucleotide sequence of SEQ ID NO:2 with the following modifications:

a) replacing the condon encoding alanine at positions 4–6, 34–36, 319–321, 535–537 or 625–627 with a condon encoding threonine;

b) replacing the codon encoding threonine at position 10–12 or 484–486 with a codon encoding alanine;

c) replacing the codon encoding valine at position 1–3 or isoleucine at position 328–330 with a condon encoding methionine;

d) replacing the codon encoding glutamic acid at position 37–39 with a codon encoding aspartic acid;

e) replacing the codon encoding arganine at position 49–51 with a codon encoding tryptophan;

f) replacing the codon encoding alanine at position 223–225 with a codon encoding proline;

g) replacing the codon encoding serine at position 304–306 with a codon encoding leucine;

h) replacing the codon encoding glycine at position 505–507 with a codon encoding alanine;

i) replacing the codon encoding glutamic acid at position 547–549 with a codon encoding lysine;

j) replacing the codon encoding glutamine at position 673–675 with a codon encoding arginine;

k) replacing the codon encoding glycine at position 709–711 with a codon encoding glutamic acid; or l) replacing the codon encoding valine at position 808–810 with a codon encoding glycine.

In another preferred embodiment, the polydeoxynucleotide has the deoxynucleotide sequence of SEQ ID NO:2 with the following modifications:

a) replacing the codon encoding alanine at positions 34–36 with a codon encoding asparagine and optionally replacing the codon encoding glutamic acid at positions 31–39 with a codon encoding glutamine;

b) replacing the codon encoding arginine at positions 100–102 with a codon encoding asparagine and replacing the codon encoding aspartic acid at positions 106–108 with a codon encoding threonine;

c) replacing the codon encoding arginine at positions 103–105 with a codon encoding asparagine and optionally replacing the codon encoding serine at positions 109–111 with a codon encoding threonine;

d) replacing the codon encoding serine at positions 394–396 with a codon encoding asparagine and optionally replacing the codon encoding serine at positions 400–402 with a codon encoding threonine with a codon encoding threonine;

e) replacing the codon encoding aspartic acid at positions 580–582 with a codon encoding asparagine and optionally replacing the codon encoding serine at positions 586–588 with a condon encoding threonine;

f) replacing the codon encoding arginine at positions 103–105 and the codon encoding aspartic acid at positions 580–582 with a codon encoding asparagine;

g) replacing the codon encoding alanine at positions 34–36 with a codon encoding asparagine, optionally replacing the codon encoding glutamic acid at positions 37–39 with a codon encoding glutamine, replacing the codon encoding aspartic acid at positions 580–582 with a codon encoding asparagine and optionally replacing the codon encoding serine at positions 586–588 with a condon encoding threonine;

h) replacing the codon encoding arginine at positions 100–102 with a codon encoding asparagine, replacing the codon encoding aspartic acid at positions 106–108 with a codon encoding threonine, replacing the codon encoding aspartic acid at positions 580–582 with a codon encoding asparagine and optionally replacing the codon encoding serine at positions 586–588 with a condon encoding threonine;

i) replacing the codon encoding arginine at positions 103–105 and aspartic acid at positions 580–582 with a codon encoding asparagine and replacing the codon encoding serine at positions 109–111 and/or positions 586–588 with a codon encoding threonine;

j) replacing the codon encoding arginine at positions 652–654 with a codon encoding glutamine, k) replacing the codon encoding glycine at position 76–78 with a codon encoding aspartic acid, and replacing the codon encoding serine at position 394–396 with a codon encoding asparagine;

l) replacing the codon encoding alanine at position 34–36 with a codon encoding asparagine, replacing the codon encoding serine at position 394–396 with a codon encoding asparagine, and replacing the codon encoding serine at position 400–402 with a codon encoding threonine; or m) replacing the codon encoding threonine at position 646–648 with a codon encoding proline and replacing the codon encoding arginine at position 652–654 with a codon encoding glutamine, The polydeoxynucleotide fragments of the present invention comprise deoxynucleotides 145–495 of the polydeoxynucleotides described above and encode modified FLINT polypeptide fragments. One example of a preferred fragment is a polydeoxynucleotide consisting of amino acids 1 through 654 of SEQ ID NO:2, modified as described above.

The present invention also includes the polydeoxynucleotides and fragments thereof described above, modified so that the codon encoding glyince at the positions corresponding to 640–642 of SEQ ID NO:2 is replaced with a codon encoding alanine.

A polydeoxynucleotide derivative comprises a polydeoxynucleotide of the present invention or a fragment thereof. The polydeoxynucleotide or fragment has an additional oligodexoynucleotide added onto the 3' and/or 5' end. An "oligopolydeoxynucleotide" is a chain of from three to about 150 deoxynucleotides. Suitable oligodeoxynucleotides are those which do not substantially detract from the ability of the polydexoynucleotide to be translated into a functional protein having about equal or increased ability compared with FLINT to inhibit FAS/FAS Ligand binding and the same or improved pharmacological and pharmaceutical properties compared with FLINT. Examples of suitable oligodeoxynucleotides include start codons, stop codons, promoter sequences, enhancer sequences and oligodeoxynucleotides encoding leader sequences or oligopeptides which improve stability or persistence in host cells or which facilitate purification.

A FLINT cDNA can be synthesized by RT-PCR method using conventional techniques. PolyA RNA is prepared from a tissue source known to express the FLINT gene (e.g. lung), using standard methods. First strand FLINT cDNA synthesis is achieved in a reverse transcriptase reaction using a FLINT sequence derived "downstream" primer. A commercially available kit such as GENEAMP by Perkin Elmer may be employed. In a subsequent PCR, FLINT specific forward and reverse primers (SEQ ID NO:1) are used to amplify the cDNA.

The amplified sample may be analyzed by agarose gel electrophoresis to check the length of the amplified. fragment (~903 base pairs). Wild-type FLINT cDNA generated in this manner is then used as a template for introduction of point mutations (i.e. construction of FLINT analogs). The basic protocol described in details in "Current Protocols in Molecular Biology", volume 1, section 8.5.7 (John Wiley and Sons, Inc. publishers), the entire teachings of which are incorporated herein by reference. In this protocol, synthetic oligonucleotides are designed to incorporate a point mutation at one end of an amplified fragment. Following first PCR, the amplified fragments encompassing the mutation are annealed with each other and extended by mutually primed synthesis. Annealing is followed by a second PCR step utilizing 5' forward and 3' reverse end primers in which the entire mutagenized fragment gets amplified and is ready for subcloning into the appropriate vector.

The present invention also relates to vectors that include isolated polydeoxynucleic acid molecules of the present invention, host cells that are genetically engineered with the recombinant vectors, and the production of modified FLINT polypeptides, modified FLINT polypeptides fragments, fusion proteins represented by Structural Formula (I) and FLINT peptide derivatives by recombinant techniques, as is well known in the art. See, e.g., Sambrook, et al., 1989; Ausubel, et al., 1987–1998, which is entirely incorporated herein by reference.

"Vector" refers to a nucleic acid compound used for introducing exogenous or endogenous nucleic acid into host cells. A vector comprises a polydeoxynucleotide sequence which may encode one or more modified FLINT polypeptides, modified FLINT polypeptides fragments, FLINT fragments, fusion proteins represented by Structural Formula (I) and FLINT peptide derivatives. Plasmids, cosmids, viruses and bacteriophages, in a natural state or which have undergone recombinant engineering, are non-limiting examples of commonly used vectors to provide recombinant vectors comprising at least one desired isolated nucleic acid molecule.

"Host cell" refers to any eucaryotic, procaryotic, or fusion or other cell or pseudo cell or membrane-containing construct that is suitable for propagating and/or expressing an isolated nucleic acid that is introduced into a host cell by any suitable means known in the art (e.g., but not limited to, transformation or transfection, or the like), or induced to express an endogenous polydeoxynucleic acid encoding a modified FLINT polypeptide, modified FLINT polypeptide fragments, fusion protein represented by Structural Formula (I) or FLINT peptide derivative according to the present invention. The cell can be part of a tissue or organism, isolated in culture or in any other suitable form.

The polydeoxynucleotides can optionally be joined to a vector containing a selectable marker for propagation in a host. Generally, a plasmid vector is introduced in a precipitate, such as a calcium phosphate precipitate, or in a complex with a charged lipid (e.g., lipofectamine). If the vector is a virus, it can be packaged in vitro using an appropriate packaging cell line and then transduced into host cells.

The DNA insert should be operatively linked to an appropriate promoter, such as the phage lambda PL promoter, phage T7 promoter, the *E. coli* lac, trp and tac promoters, the SV40 early and late promoters and promoters of retroviral LTRs, or any other suitable promoter. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UGA and UAA preferred for mammalian or eukaryotic cell expression.

Expression vectors will preferably include at least one selectable marker. Such markers include, e.g., dihydrofolate reductase, neomycin, zeocin, hygromycin B or puromycin resistance for eukaryotic cell culture, and tetracycline or ampicillin resistance genes for culturing in *E. coli* and other bacteria or prokaryotics. Representative examples of appropriate hosts include, but are not limited to, bacterial cells, such as *E. coli, Streptomyces, Bacullus subtilis* and *Salmonella typhimurium* cells; yeast cells such as *Saccharomyces cervisiae, Saccharomyces pombe* or *Pichia pastoris*; insect cells such as *Drosophila* S2 *Spodoptera* Sf9 cells or Sf21 and High Five (BTI-TN-5B1–4) cells; animal cells such as 293, 293 EBNA, CHO, COS and COS7, BHK, AV12 and Bowes melanoma cells; and plant cells. Appropriate culture mediums and conditions for the above-described host cells are known in the art. Vectors preferred for use in bacteria include pET15 and pET30 available from Novagen pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Preferred eucaryotic vectors include pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of a vector construct into a host cell can be effected by calcium phosphate transfection, DEAE-dextran mediated transfection, cationic lipid-mediated transfection, electroporation, transduction, infection or other methods. Such methods are described in many standard laboratory manuals, such as Sambrook, supra, Chapters 1–4 and 16–18; Ausubel, supra, Chapters 1, 9, 13, 15, 16, the entire relevant teachings of which are incorporated herein by reference.

The modified FLINT polypeptides, modified FLINT polypeptide fragments, FLINT fragments, fusion protein represented by Structural Formula (I) and FLINT peptide derivatives of the present invention can be expressed in a modified form, such as a fusion protein or a "tagged" protein. For instance, a region of additional amino acids, particularly hexahistidine ($His_6$) tag, can be added to the carboxy terminus of a polypeptide to facilitate purification. Such regions can be removed prior to final preparation of a polypeptide. They can be secreted by virtue of heterologous secretion signals (such as mouse Ig in vector pSecTag2. Such methods are described in many standard laboratory manuals, such as Sambrook, supra, Chapters 17.29–17.42 and 18.1–18.74; Ausubel, supra, Chapters 16, 17 and 18, the entire relevant teachings of which are incorporated herein by reference.

Fc Fusions

The present invention also relates to fusion proteins comprising an Fc fragment of an immunoglobulin molecule fused to FLINT or FLINT analog including, for example, a FLINT fragment such as the FLINT metabolite comprising residues 1 to 218 of SEQ ID NO:1, and further including, for example, a protease-resistant FLINT analog, such as R218Q.

The Fc FLINT constructs of the present invention show increased half-lives compared to native FLINT or FLINT analog that is not embodied as an Fc fusion. For example, Fc R218Q FLINT showed a half life of approximately 3 hours in CD-1 mice, versus a half life of about 30 minutes for R218Q after IV administration (10 ug/mouse).

One example of a suitable Pc Fragment is an Fc Fragment with a truncation of from one to about fifteen amino acids from the N-terminal ends of the two heavy chains, preferably from about five to about fifteen amino acids. Another example of an analog of an Fc Fragment is an Fc Fragment with one or more point mutations which do not substantially increase of the affinity of the analog for complement compared with the Fc Fragment. The amino acid sequence of an Fc analog preferably has greater than about 95% homology with the Fc Fragment, more preferably greater than about 99%. Examples of preferred point mutations include the replacement of one or more cysteines with serine or replacement of one or more amino acids in the hinge region. Analogs of the Fc Fragment can be prepared by methods disclosed in Strom et al., WO 99/02711, the entire teachings of which are incorporated herein by reference.

European Patent Application EP-A-0 464 533, herein incorporated by reference, discloses fusion proteins comprising various portions of the constant region of immunoglobulin molecules, together with an heterologous human protein, or part thereof.

The present invention provides a soluble Fc fusion protein having FLINT activity, comprising an FLINT or FLINT analog fused to at least one human immunoglobulin constant domain or fragment thereof.

As used herein, "FLINT activity" means, for example, anti-apoptotic activity, in an in vitro or in vivo assay.

The immunoglobulin portion of the fusion may be of any subclass (IgG, IgM, IgA, IgE), but is preferably IgG, such as IgG1, IgG3 or IgG4. The constant domain(s) or fragment thereof may be derived from the heavy or light chain or both.

The invention encompasses mutations, substutions, additions, and/or deletions in the immunoglobulin component which eliminate undesirable properties of the native immunoglobulin, such as Fc receptor binding and/or introduce desirable properties such as stability. For example, Angal S., King D. J., Bodmer M. W., Turner A., Lawson A. D. G., Roberts G., Pedley B. and Adair R., Molecular Immunology, 30, 105–108(1993), describe an IgG4 molecule where residue 241 (Kabat numbering) is altered from serine to proline. This change increases the serum half-life of the IgG4 molecule. Canfield S. M. and Morrison S. L., Journal of Experimental Medicine, 173,1483–1491, describe the alteration of residue 248 (Kabat numbering) from leucine to glutamate in IgG3, and from glutamate to leucine in mouse IgG2b. Substitution of leucine for glutamate in the former decreases the affinity of the immunoglobulin molecule concerned for the Fc gamma RI receptor, and substitution of glutamate for leucine in the latter increases the affinity. EP0307434 discloses various mutations including an L to E mutation at residue 248 (Kabat numbering) in IgG.

Preferably, a fusion molecule of the present invention lacks the hinge region, or alternatively comprises subregions therefrom. In preliminary experiments Applicants determined that FLINT-Fc fusion proteins had a propensity to aggregate to produce multimeric species larger than a dimer as judged by Western blot analysis. Such aggregated species were inactive in an in vitro cell-based apoptosis assay. Subsequent purification of the multimeric aggregates over a protein A column with elution under acidic conditions failed to disaggregate the protein. Applicants hypothesized that decreasing the conformational mobility of the fusion protein might alleviate the aggregation problem. To test this, fusion constructs were made having more rigidity by progressive deletions within the 15 amino acid hinge region. The following constructs were prepared and tested in an in vitro apoptosis assay.

| FLINT Fc Plasmid | FLINT Fusion | Description |
| --- | --- | --- |
| FLINT:Fc(minus CH1)/pmEAK | FL:Fc-CH1 | FLINT-Fc (15 AA hinge, CH2, CH3) |
| FLINT:Fc(plus Thrombin/minus CH1)/pmEAK | FL:Fc + T-CH1 | FLINT-Fc (LVPRGS linker, hinge, CH2, CH3) |
| FLINT:Fc(minus 5AA hinge)/pmEAK | FL:Fc-5AA hinge | FLINT-Fc (10 AA hinge, CH2, CH3) |
| FLINT:Fc(minus hinge)/pmEAK | FL:Fc-hinge | FLINT-Fc (no hinge, CH2, CH3) |
| FLINT:Fc(plus thrombin/minus hinge)/pmEAK | FL:Fc + T-hinge | FLINT-Fc (LVPRGS linker, CH2, CH3) |

The sequence "LVPRGS" which is present in several constructs, encodes a thrombin cleavage site that is found in many commercially available vectors useful for expressing fusion proteins. The Fc constructs were expressed transiently in 293EBNA cells and the conditioned media used in the bioassay. These experiments showed that the FL:Fc-hinge and FL:Fc+T hinge constructs were active in inhibiting apoptosis in vitro while the other constructs were less active. Presumably deletion of all or part of the hinge region prevents the higher aggregation that is observed when the full hinge region is present.

In another aspect the IgG component is derived from IgG4, comprising the CH2 and CH3 domains and the hinge region including cysteine residues contributing to inter-heavy chain disulphide bonding, for example residues 8 and 11 of the IgG4 hinge region (Pinck J. R. and Milstein C., Nature vol216pp941–942, 1967). The IgG4 component may consist of amino acids corresponding to residues 1–12 of the hinge, 1–110 of CH2 and 1–107 of CH3 of IgG4 described by Ellison J., Buxbaum J. and Hood L., DNA, 1, 11–18, 1981.

Fusion of FLINT or FLINT analog to the Ig constant domain or fragment is by C-terminus of one component to N-terminus of the other. Preferably FLINT or analog thereof is fused via its C-terminus to the N-terminus of the Ig constant domain or fragment.

In a further aspect, the invention provides a process for preparing a compound according to the invention which process comprises expressing DNA encoding said compound in a recombinant host cell and recovering the product.

Expression of Proteins in Host Cells

Using polydeoxynucleotides of the present invention, one may express a modified FLINT polypeptides, modified FLINT polypeptide fragments, FLINT fragments, fusion protein represented by Structural Formula (I), and FLINT peptide derivatives of the present invention in a recombinantly engineered cell, such as bacteria, yeast, insect, or mammalian cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a modified FLINT polypeptides, modified FLINT polypeptide fragment, fusion protein represented by Structural Formula (I) or FLINT peptide derivative of the present invention. No attempt to describe in detail the various methods known for the expression of proteins in prokaryotes or eukaryotes will be made.

In brief summary, the expression of isolated nucleic acids encoding a modified FLINT polypeptide, modified FLINT polypeptide fragment, fusion protein represented by Structural Formula (I) or FLINT peptide derivative of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification handle sequences.

Alternatively, polydeoxynucleotides of the present invention can be expressed in a host cell by turning on (by manipulation) in a host cell that contains endogenous DNA encoding a modified FLINT polypeptides, modified FLINT polypeptide fragments, fusion protein represented by Structural Formula (I) or FLINT peptide derivatives of the present invention. Such methods are well known in the art, e.g., as described in U.S. Pat. Nos. 5,580,734, 5,641,670, 5,733,746, and 5,733,761, entirely incorporated herein by reference.

Expression in Prokaryotes

Prokaryotic cells may be used as hosts for expression. Prokaryotes most frequently are represented by various strains of E. coli; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., Nature 198:1056 (1977)), the tryptophan (trp) promoter system (Goeddel, et al., Nucleic Acids Res. 8:4057 (1980)), T7 phage promoter (Studier, F. W., Methods in Enzymology, 185, 60–89, (1990),and the lambda derived P L promoter and N-gene ribosome binding site (Shimatake, et al., Nature 292:128 (1981)), the teachings of which are incorporated herein by reference. The inclusion of selection markers in DNA vectors transfected in E. coli is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transformed with the plasmid vector DNA. Expression systems for expressing a protein of the present invention are available using Bacillus subtilis and Salmonella (Palva, et al., Gene 22:229–235 (1983); Mosbach, et al., Nature 302:543–545 (1983)), the teachings of which are incorporated herein by reference.

Expression in Eukaryotes

A variety of eukaryotic expression systems such as yeast, insect cell lines, plant and mammalian cells, are known to those of skill in the art. As explained briefly below, a polydeoxynucleotide of the present invention can be expressed in these eukaryotic systems.

Synthesis of heterologous proteins in yeast is well known. F. Sherman, et al., Methods in Yeast Genetics, Cold Spring Harbor Laboratory (1982), the teachings of which are incorporated herein by reference, is a well-recognized work describing the various methods available to produce the protein in yeast. Two widely utilized yeast for production of eukaryotic proteins are Saccharomyces cerevisiae and Pichia pastoris. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A modified FLINT polypeptide, modified FLINT polypeptide fragment, fusion protein represented by Structural Formula (I) or FLINT peptide derivative of the present invention, once expressed, can be isolated from yeast by applying standard protein isolation techniques. The monitoring of the purification process can be accomplished by using SDS polyacrylamide gel electrophoresis (SDS-PAGE), Western blot techniques or radioimmunoassay of other standard immunoassay techniques such as ELISA.

The sequences encoding modified FLINT polypeptides, modified FLINT polypeptide fragments, FLINT fragments, fusion proteins represented by Structural Formula (I) or FLINT peptide derivatives of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the AV12, HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., Immunol. Rev. 89:49 (1986), the entire teachings of which are incorporated herein by reference), and processing information sites, such as ribosome binding sites, RNA splice sites, polyadenylation sites (e.g., bovine growth hormone poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing modified FLINT polypeptides, modified FLINT polypeptide fragments, fusion protein represented by Structural Formula (I) or FLINT peptide derivatives of the present invention in insect cells a are usually derived from the SF9 baculovirus. Suitable insect cell lines include mosquito larvae, silkworm, armyworm, moth and Drosophila cell lines such as a Schneider cell line (See Schneider, J. Embryol. Exp. Morphol. 27:353–365 (1987), the entire teachings of which are incorporated herein by reference).

As with yeast, when higher animal or plant host cells are employed, polyadenlyation or transcription terminator sequences are typically incorporated into the vector. An example of a terminator sequence is the polyadenlyation sequence from the bovine growth hormone gene. sequences for accurate splicing of the transcript may also be included. An example of a splicing sequence is the VP1 intron from SV40 (Sprague, et al., J. Virol. 45:773–781 (1983), the entire teachings of which are incorporated herein by reference). Additionally, gene sequences to control replication in the host cell may be incorporated into the vector such as those found in bovine papilloma virus type-vectors. M. Saveria-Campo, Bovine Papilloma Virus DNA, a Eukaryotic Cloning Vector in DNA Cloning Vol. II, a Practical Approach, D. M. Glover, Ed., IRL Press, Arlington, VA, pp. 213–238 (1985), the entire teachings of which are incorporated herein by reference.

Protein Purification

A modified FLINT polypeptides, modified FLINT polypeptide fragments, FLINT fragments, fusion protein represented by Structural Formula (I) or FLINT peptide derivatives can be recovered and purified from lysed cells (e.g, E. Coli) or recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. Polypeptides of the present invention include naturally purified products, products of chemical synthetic procedures, and products produced by recombinant techniques from a prokaryotic or eucaryotic host, including, for example, bacterial, yeast, higher plant, insect and mammalian cells. Depending upon the host employed in a recombinant production procedure, the polypeptides of the present invention can be glycosylated or can be non-glycosylated. In addition, polypeptides of the invention can also include an initial modified methionine residue, in some cases as a result of host-mediated processes. Such methods are described in many standard laboratory manuals, such as Sambrook, supra, Chapters 17.37–17.42; Ausubel, supra, Chapters 10, 12, 13, 16, 18 and 20, the entire relevant teachings of which are incorporated herein by reference.

Modified FLINT polypeptides, modified FLINT polypeptide fragments, FLINT fragments, and FLINT peptide derivatives are believed to inhibit the binding of FAS to FAS Ligand and LIGHT to LTβR and TR2/HVEM receptors, and can therefore be used to treat subjects with a disease and/or condition associated with such binding, e.g., when FAS is activated to a greater extent than normal or is inappropriately activated by FAS Ligand. Flint analogs which inhibit FAS/FAS Ligand binding show activity in the assay described in Example 11.

Runaway apoptosis is one example of a condition caused by excessive activation of FAS by FAS/FAS Ligand signal transduction pathway and which can be treated with the Flint analogs of the present invention (see U.S. Provisional Application Ser. No. 60/112,577, filed Dec. 18, 1998, Kondo et al., Nature Medicine 3(4):409–413 (1997) and Galle et al., J. Exp. Med. 182:1223–1230 (1995), the entire teachings of which are incorporated herein by reference). Runaway apoptosis can cause pathological conditions such as organ failure in the subject. Diseases associated with runaway apoptosis include, but are not limited to, acute liver failure (e.g., liver failure associated with viral infections affecting the liver, bacterial infections affecting the liver, hepatitis, hepatocellular injury and/or other conditions where hepatocytes undergo massive apoptosis or destruction), kidney failure and failure of pancreatic function. Flint analogs which inhibit runaway apoptosis generally show activity in the Jurkat cell assay described in Example 8 and in the in vivo assay for liver damage described in Example 11.

The FLINT analogs of the present invention are generally therapeutically useful for diseases which can be treated with FLINT. (See U.S. patent application Ser. No. 09/280,567; and Miwa et al., Nature Medicine 4:1287 (1998), the entire teachings of which are incorporated herein by reference). One example is inflammation caused by FAS Ligand induced neutrophil activation Inflammatory disease associated with neutrophil activation include sepsis, ARDS, SIRS and MODS. FLINT analogs which show activity in the in vivo assay described in Example 12 generally inhibit neutrophil activation.

Other diseases for which FLINT has been shown to be therapeutically useful include Rheumatoid arthritis (Elliott et al., Lancet 344:1105–10 (1994)), acute lung injury, ARDS, fibroproliferative lung disease, fibrotic lung disease, HIV (Dockrell et al., J. Clin. Invest. 101:2394–2405 (1998)), Ischemia (Sakurai et al. 1998 Brain Res 797:23–28), Brain trauma/injury (Ertel et al. 1997 J Neuroimmunol 80:93–6), chronic renal failure (Schelling et al. 1998 Lab Invest 78:813–824), Graft-vs-Host Disease (GVHD) (Hattori et al. 1998 Blood 11:4051–4055), Cutaneous inflammation (Orteu at al. 1998 J Immunol 161:1619–1629), Vascular leak syndrome (Rafi et al. 1998 J Immunol 161:3077–3086), Helicobacter pylori infection (Rudi et al. 1998 J Clin Invest 102:1506–1514), Goiter (Tamura et al. 1998 Endocrinology 139:3646–3653), Atherosclerosis (Sata and Walsh, 1998 J Clin Invest 102:1682–1689), IDDM (Itoh et al. 1997 J Exp Med 186:613–618), Osteoporosis (Jilka et al. 1998 J Bone Min Res 13:793–802), Crohn's Disease (van Dullemen et al. 1995 Gastroenterology 109:129–35), Transplant (graft) rejection (Lau et al. 1996 Science 273:109–112), Sepsis (Faist and Kim. 1998 New Horizons 6:S97–102), Pancreatitis (Neoptolemos et al. 1998 Gut 42:886–91), Cancer (melanoma, colon and esophageal) (Bennett et al. 1998 J Immunol 160:5669–5675), Autoimmune disease (IBD, psoriasis, Down's Syndrome (Seidi et al., *Neuroscience Lett.* 260:9 (1999) and multiple sclerosis (D'Souza et al. 1996 J Exp Med 184:2361–70).

Co-pending U.S. Patent Application entitled THERAPUETIC APPLICATIONS OF FLINT POLYPEPTIDES, filed Mar. 30, 1999 Ser. No. 09/280,567, discloses other disease which can be treated with the FLINT analogs of the present invention. Examples include Alzheimer's Disease; Acute respiratory disease syndrome; End-stage renal disease (ESRD); mononulceosis; EBV; Herpes; ulcerative colitis; antibody dependent sytotoxicity; hemolytic and hypercoagulation disorders such as vascular bleeds, DIC (disseminated intervascular coagulation), eclampsia, HELLP (preeclampsia complicated by thrombocytopenia, hemolysis and disturbed liver function), HITS (heparin induced thrombocytopenia), HUS (hemolytic uremic syndrome), and preeclampsia; hematopoeitic disorders such as aplastic anemia, thrombocytopenia (TTP) and myelodysplasia; and hemolytic fever caused, for example, by *E.bola*. The ability of FLINT and FLINT analogs to retard apoptosis under ischemic conditions is useful also in preserving organs and tissues harvested for transplantation. Ischemic conditions include, but are not limited to, neuronal ischemia, limb crush injuries, spinal cord injuries, myocardial infarct including acute, subacute and chronic sequelae and related clinical syndromes, congestive heart failure. Also, innocent bystander tissues which are damaged during chemotherapy, radiation therapy, toxic drugs, trauma, surgery and other stresses can be treated with FLINT. One example of such a disease is mucositis which can be a life-threatening side-effect of cancer treatment.

Acute Lung Injury and Acute Respiratory Distress Syndrome

Acute lung injury (ALI) and acute respiratory distress syndrome (ARDS) represent disease entities that differ only in the severity of the hypoxemia present at diagnosis. A widely accepted parameter for diagnosis is the PaO2 to FiO2 ratio, according to which ARDS patients manifest a ratio of less than or equal to 200 mm Hg, whereas ALI patients exhibit values of less than or equal to 300 mm Hg. ARDS represents a more severe form of ALI. Numerous mediators are likely to contribute to the pathogenesis of ARDS/ALI with neutrophils playing a prominent role. While multiple precipitating factors are probable in the development of ARDS, both direct and indirect, the major cause appears to be sepsis and the systemic inflammatory response syndrome, accounting for approximately 40% of cases. Mortality in ARDS is high approximating 40%, with most deaths occurring within the first 2 to 3 weeks. There is no currently available, approved pharmacologic therapy for ARDS and treatment at present is limited to aggressive supportive care.

There is evidence that ARDS may be mediated by soluble FasL/Fas interaction in humans (Matute-Bello et al., J. Immunol. 163, 2217–2225, 1999). FLINT, by binding to FasL, could inhibit FasL-mediated pneumocyte or endothelial cell apoptosis, thus inhibiting or preventing the progression from acute inflammatory insult to ALI, and from ALI to ARDS.

In one embodiment the present invention relates to the use of FLINT to inhibit and/or treat ALI and/or ARDS comprising the administration of a therapeutically effective amount of FLINT to a person in need thereof.

Chronic Obstructive Pulmonary Disease (COPD)

Chronic obstructive pulmonary disease (COPD) is the fourth leading cause of non-accidental death in the US following heart disease, cancer and cerebral vascular disease. COPD is an obstructive airway disorder encompassing multiple conditions including chronic bronchitis, emphysema, bronchiectasis, and chronic asthma. COPD is slowly progressive and produces an irreversible decline in lung function. Chronic hypoxemia and hypercapnia are the eventual outcomes of the disorder. The mechanism by which COPD disrupts lung function appears to involve dysregulated apoptosis. Plasma samples from patients suffering from COPD exhibit higher concentrations of soluble Fas compared with healthy control subjects (See Yasuda et al. Resp. Med. 92, 993–999, 1998). The increased levels of soluble Fas in COPD patients may reflect increased Fas-induced apoptosis.

In another embodiment, the present invention relates to the use of FLINT to treat and/or inhibit COPD in a patient in need thereof by administering a therapeutically effective amount of FLINT.

Pulmonary Fibrosis (PF)

Pulmonary fibrosis (also known as fibrosing lung disease) occurs as an end result of the process of attempted healing during acute or chronic lung injury. The pathological mechanism of such lung injury can be any of various factors that first trigger an inflammatory response in the alveoli or surrounding interstitium and subsequently trigger alveolar/interstitial fibrosis (i.e. the repair response). Fibrosis in other tissues such as the epidermis or the peritoneum, leads to visible scarring or adhesions, respectively. Pulmonary fibrosis, in contrast, leads to restrictive lung disease (decreased lung capacities and decreaased oxygen diffusion). Conditions associated with pulmonary fibrosis include but are not limited to: idiopathic pulmonary fibrosis, connective tissue diseases (e.g. lupus, scleroderma), drug-induced lung disease (e.g. bleomycin), pneumoconioses (e.g. asbestosis), sarcoidosis, eosinophilic granulomatosis, hypersensitivity pneumonitis, and other diseases asscoiated with severe lung inflammation that can result in acute lung injury and/or acute respiratory distress syndrome (e.g. trauma, sepsis, near-drowning, gastric aspiration, shock, etc.). Fibrosis of the airways is also a feature of the chronic inflammation in COPD.

The etiology of PF may involve FasL/Fas-triggered apoptosis. Indeed, an intact FasL/Fas system is essential in the etiology of bleomycin-induced PF in mice (See Kuwano K. et al. J. Clin. Invest. 104, 13–19 (1999).

In another embodiment the present invention relates to the use of a FLINT analog to inhibit and/or treat PF. For example, FLINT analog can be administered acutely at the time of an inflammatory insult to the lung (e.g. during bleomycin treatment) to prevent PF from occurring.

A "subject" is a mammal in need of treatment, preferably a human, but can also be an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

An "effective amount" of a FLINT analog is an amount which results in a sufficient inhibition of one or more processes mediated by the binding of FAS to FAS Ligand, or LIGHT to LTAR and/or TR2/HVEM so as to achieve a desired therapeutic or prophylactic effect in a subject with a disease or condition associated with aberrant FAS/FAS Ligand binding and/or LIGHT mediated binding. One example of such a process is runaway apoptosis. Alternatively, an "effective amount" of a FLINT analog is a quantity sufficient to achieve a desired therapeutic and/or prophylactic effect in a subject with inflammation caused by FAS Ligand induced neutrophil activation or any of the other aforementioned diseases associated with aberrant FAS Ligand activity.

A "desired therapeutic and/or prophylactic effect" in a subject with a disease or condition includes the amelioration of symptoms or delay in onset of symptoms associated with such disease. Alternatively, a "desired therapeutic and/or prophylactic effect" includes an increased survival rate or increased longevity for the subject with the disease. The amount of FLINT analog administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors.

As a general proposition, the total pharmaceutically effective amount of the FLINT analogs of the present invention administered parenterally per dose will be in the range of about 1 µg/kg/day to 10 mg/kg/day of patient body weight, particularly 2 mg/kg/day to 8 mg/kg/day, more particularly 2 mg/kg/day to 4 mg/kg/day, even more particularly 2.2 mg/kg/day to 3.3 mg/kg/day, and finally 2.5 mg/kg/day, although, as noted above, this will be subject to therapeutic discretion. More preferably, this dose is at least 0.01 mg/kg/day. If given continuously, the FLINT analogs of the present invention are typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the FLINT analogs of the present invention may be administered orally, rectally, intracranially, parenterally, intracisternally, intravaginally, intraperitoneally, topically (as by powders, ointments, drops or transdermal patch), transdermally, intrathecally, bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein includes, but is not limited to, modes of administration which include intravenous, intramuscular, intraperitoneal, intrasternal, subcutaneous and intraarticular injection, infusion and implants comprising FLINT analogs.

The FLINT analogs of the present invention are also suitably administered by sustained-release systems. Suitable examples of sustained-release compositions include semipermeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R.Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988). Other sustained-release compositions also include liposomally entrapped modified FLINT polypeptides, FLINT peptide fragments and FLINT peptide derivatives. Such liposomes are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EDP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal TNFR polypeptide therapy.

For parenteral administration, in one embodiment, the FLINT analogs of the present invention are formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the FLINT analogs of the present invention uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The FLINT analogs of the present invention are typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of salts of the FLINT analogs of the present invention.

Polypeptides to be used for therapeutic administration must be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

FLINT analogs ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution of one of the FLINT analogs of the present invention, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the FLINT analogs of the present invention may be employed in conjunction with other therapeutical compounds.

In the case of organ preservation in preparation for harvesting, for instance, FLINT is useful prophylactically to prevent the apoptosis associated with ischemia reperfusion injury to the organ once it is removed from the donor. In one embodiment of this aspect of the invention, FLINT is administered to the organ donor prior to harvesting the organ. After harvesting the organ, FLINT is added to a suitable medium for transport/storage of the organ. Alternatively, the harvested organ is perfused with a medium containing FLINT prior to transplantation into a recipient. Suitable media for this purpose are known, for example, the media disclosed in EP 0356367 A2, herein incorporated by reference. The method may also include treating the transplant recipient with FLINT prior to and/or after the transplant surgery.

A typical method involves pre-treating the organ donor with an effective amount of FLINT prior to organ harvesting. Alternatively, or conjunctively, the harvested organ may be perfused or bathed in a FLINT-containing solution. This method may be employed, for example, with kidney, heart, lung and other organs and tissues.

The FLINT analogs of the present invention have utilities other than for therapy. For example, these FLINT analogs can be used as research tools to predict how certain amino acid substitutions influence, positively or negatively, the properties of TNFR proteins such as FLINT and their homolgues, e.g., 1) the ability of such proteins to bind their ligands; and 2) the pharmaceutical properties of such proteins and their homologues. Because FLINT is homologous to TNFR proteins, it is expected that a point mutation which effects a property of FLINT would have a similar effect when the corresponding mutation is made in a TNFR protein or homologue thereof. Thus, the FLINT analogs of the present invention can be used together with homology models of TNFR proteins to predict the effect of certain point mutations on the properties of TNFR proteins.

The invention is illustrated by the following examples which are not intended to be limiting in any way.

EXEMPLIFICATION

Example 1

Production of a Vector for Expressing FLINT Analogs in a Prokaryotic Expression System An expression vector suitable for expressing FLINT or analogs thereof in a variety of prokaryotic host cells, such as *E. coli* is easily made. The vector contains an origin of replication (Ori), an kanamycin resistance gene (Amp) useful for selecting cells which have incorporated the vector following a transformation procedure, and further comprises the T7 promoter and T7 terminator sequences in operable linkage to a FLINT coding region. Plasmid pET30a (obtained from Novogen, Madison Wis.) is a suitable parent plasmid. PET30a is linearized by restriction with endonucleases NdeI and BamHI. Linearized pET30a is ligated to a DNA fragment bearing NdeI and BamHI sticky ends and comprising the coding region of the FLINT gene as disclosed by SEQ ID NO:1 or a fragment thereof.

The FLINT gene used in this construction is slightly modified at the 5' end (amino terminus of encoded polypeptide). FLINT site-directed mutants are constructed based on the protocol described in the reference:, Saiki, R., K., et al. *Science* 239:487–491 (1988) and quoted in a comprehensive manual "Current Protocols in Molecular Biology", volume 1, section 8.5.7 (John Wiley and Sons, Inc. publishers). The entire teachings of these references are incorporated herein by reference. Silent mutations are introduced in the gene such as ones to generate unique restriction sites that can facilitate "cassette" transfer of FLINT analogs from prokaryotic to eukaryotic expression vectors.

Example 2

Prokaryotic Expression and Purification of Recombinant FLINT Analogs

An expression vector that carries an open reading frame (ORF) encoding FLINT or analog thereof and which ORF was properly linked to an expression promoter is transformed into competent *E. coli* strain BL21 (DE3)(hsdS gal cIts857 ind1Sam7nin5lacUV5-T7gene 1)available from Novogen (Madison Wis.) using standard methods. Multiple transformants, selected for resistance to kanamycin, were chosen at random and used to inoculate LB/kanamycin media. Cultures were grown at 37° C. with shaking to cell density of $OD_{600}$=0.8–1.0 at which point FLINT protein synthesis was induced with 1 mM IPTG. Cultures were grown at 37° C. for 3h postinduction before the cells are harvested. FLINT analog product encoded by the vector-borne ORF was purified from the fit insoluble fraction of cell lysate, the inclusion bodies. In brief, the purification consisted of inclusion bodies preparation and solubilization, and protein refolding followed by cation-exchange and size-exclusion chromatography procedures, respectively.

Example 3

Construction of Vector for Expression of FLINT Analogs in Mammalian Cells

A bicistronic expression vector are constructed by insertion of an "internal ribosome entry site"/enhanced green fluorescent polypeptide (IRES/eGFP) PCR fragment into the mammalian expression vector pGTD (Gerlitz, B. et al., 1993, Biochemical Journal 295:131). This new vector, designated pIG1, contains the following sequence landmarks: the E1a-responsive GBMT promoter (D. T. Berg et al., 1993 BioTechniques 14:972; D. T. Berg et al., 1992 Nucleic Acids Research 20:5485); a unique BclI cDNA cloning site; the IRES sequence from encephalomyocarditis virus (EMCV); the eGFP (Clontech) coding sequence (Cormack, et al., 1996 Gene 173:33); the SV40 small "t" antigen splice site/polyadenylation sequences; the SV40 early promoter and origin of replication; the murine dihydrofolate reductase (dhfr) coding sequence; and the pBR322 ampicillin resistance marker/origin of replication.

Based on the human FLINT cDNA sequence, the forward and reverse PCR primers are synthesized bearing BclI restriction site at their respective 5' ends. These primers are used to PCR amplify the FLINT analog cDNA. The resultant ~900 base pair PCR product is digested with BclI and ligated into the unique BclI site of pIG1 to generate the plasmid pIG1-FLINT. The human FLINT cDNA orientation and nucleotide sequence are confirmed by restriction digest and double stranded sequencing of the insert. FLINT sequence in pIG1 is modified by silent mutagenesis in order to enable "Cassette" transfer of analogs previously constructed in prokaryotic vector pET30a. It can be also modified at the C-terminus introducing a cleavable hexahistidine (His6) cassette to facilitate analog purification.

The entire teachings of the references referred to in this Example are incorporated herein by reference.

Example 4

Construction of a Vector for Expressing an Fc-Protease Resistant FLINT Analog

R218Q Fc-hinge/JB02 is a 7 kb vector constructed from a modified pEAK vector for transient expression in 293EBNA cells. The vector comprises a tk promoter, an SV40 origin of replication, and a gene encoding an R218Q Fc fusion lacking the hinge region.

Media from cells transfected with this vector was concentrated in an Amicon Pro-Flux M12 tangential filtration ten-fold using an Amicon S3Y10 UF membrane. Media containing R218Q FLINT-Fc was adjusted to 0.5 M NaCl and 5 mM EDTA. The concentrated media was passed over a Protein A HiTrap column (Pharmacia, 5 ml column) at a flow rate of 5 ml/min. The column was wahsed with buffer A (PBS, 1 mM potassim phosphate, 3 mM sodium phosphate; 0.5 M Na Cl, pH 7.4) until the absorbance returned to baseline and the bound polypeptides were eluted with 100% buffer B (50 mM citric acid, 0.5 M NaCl, pH 3.5). The eluted material was neutralized with 100 ul of 1 M Tris pH 8.0 per ml of elution buffer. Fractions containing R218Q Fc were pooled and passed over a Superdex 75 (Pharmacia, 16/60) sizing column equilibrated with PBS, 0.5 M NaCl, pH 7.4, at a flow rate of 1 ml/min. Fractions containign R218Q FLINT-Fc were analyzed by SDS PAGE. The N-terminal sequence of R218Q FLINT-Fc was confirmed on the purified polypeptide. The addition of EDTA reduces the potential of the molecule to aggregate.

Example 5

R218Q FLINT-Fc Fusion Protein Inhibits Apoptosis

When assayed in the Jurkat cell in vitro cell-based apoptosis assay, R218Q FLINT-Fc (minus hinge) demonstrated activity comparable to wild-type FLINT.

Example 6

Isolation of High-Producing FLINT Analog Clone from AV12 RGT18 Transfectants

The recombinant plasmid carrying the FLINT gene encodes resistance to methotrexate. In addition, the construct contains a gene encoding a fluorescent polypeptide, GFP, on the same transcript and immediately 3' to the FLINT gene. Since high level expression of GFP would require a high level of expression of the FLINT-GFP mRNA, highly fluorescent clones would have a greater probability of producing high levels of FLINT. AV12 RGT18 cells are transfected using calcium phosphate procedure with recombinant PIG1 plasmids containing FLINT analogs. Cells resistant to 250 nM methotrexate are selected and pooled. The pool of resistant clones is subjected to fluorescence assisted cell sorting (FACS), and cells having fluorescence values in the top 5% of the population are sorted into a pool and as single cells. The high fluorescence pools are subjected to three successive sorting cycles. Pools and individual clones from the second and third cycles are analyzed for FLINT production by SDS-PAGE. Pools or clones expressing FLINT at the highest level judged from Coomassie stained SDS-PAGE gels are used for scale-up and FLINT purification.

Example 7

Quantitation of FLINT Analogs

FLINT analogs can be quantitated in crude media of transfected cells and during purification procedure by developed FLINT ELISA. ELISA uses anti-FLINT polyclonal antibody TKD-028(1494) as a capture antibody and biotinylated anti-FLINT TKD-076A as a primary antibody in a "sandwich". ELISA is developed by strep-avidin derivatized horse radish peroxidase (SA-HRP) using OPD as a substrate and monitoring the absorbance at 490 mn. Useful range of such an ELISA is from 0.2–20 ng/ml.

Example 8

Measuring the Effect of a FLINT Analog on FasL Induced Jurkat cells Apoptosis

A FLINT bioassay measuring cell survival (i.e. prevention of apoptosis) was performed in a 96 well plate format with reactions of 100 $\mu$l/well. 25 $\mu$l of Jurkat cells ($5\times10^4$ cells/well) was mixed with 25 $\mu$l of recombinant human FasL (final concentration 150 ng/ml) and 50 $\mu$l of supernatant from transient transfections of 293EBNA cells with FLINT analogs. Cells were incubated at 37° C. overnight. Twenty $\mu$l of MTS tetrazolium compound (U.S. Pat. No. 5,185,450 assigned to the Univ. of South Florida and exclusively licensed to Promega Corporation, Madison, Wis.) were added to each well and the incubation carried out for 2h at 37° C. Absorbance at 490 nm was recorded in a plate reader. The results are shown below. All but one of the analogs exhibited anti-apoptotic activity in this assay.

| MUTANT | TYPE | INHIBITION OF APOPTOSIS |
|---|---|---|
| Wild type FLINT |  | +++ |
| A12N | CHO | ++ |
| A12N, E13Q | CHO | ++ |
| R34N, D36T | CHO | +++ |
| S132N | CHO | + |
| G26D, S132N | CHO | − |
| D194N | CHO | ++ |
| D194N, S196T | CHO | ++ |
| R34N, D36T, D194N, S196T | CHO | ++ |
| R218Q | PR | ++ |
| R218E | PR | ++ |
| T216P, R218Q | PR | ++ |
| A12N, E13Q, D194N, S196T | CHO | + |

PR = protease resistant
CHO = glycosylation analof

Example 9

Large Scale FLINT Analog Polypeptide Purification

Large scale production of FLINT analogs (containing a 6 histidine tag) was performed by growing stable clones in several 10 liter spinners. After reaching confluency, cells were further incubated for 2–3 days to secrete maximum amount of FLINT analogs into the medium. Medium containing FLINT analogs were concentrated in an Amicon ProFlux M12 tangential filtration system to 350 ml. The concentrated medium was passed over IMAC (Immobilized Metal-Affinity Chromatography(Pharmacia, 5 to 10 ml column) at a flow rate of 1 ml/min. The column was washed with buffer A(PBS, 0.5 M NaCl, pH 7.4) until the absorbency (280 nm) returned to baseline and the bound polypeptides were eluted with a linear gradient from 0.025 M–0.5 M Imidazol(in buffer A) developed over 60 min. Fractions containing the FLINT analog were pooled and concentrated to 2 ml using an Ultrafree centrifugal filter unit (Millipore). The recovered material was passed over a 16/60 Superdex 200 sizing column (Pharmacia) equilibrated with PBS, 0.5 M NaCl, 10% glycerol, pH 7.4. Fractions containing the FLINT analog were analyzed by SDS-PAGE. The N-terminal sequence of FLINT was confirmed on the purified polypeptide.

Example 10

Biophysical Characterization of Purified FLINT Analogs

FLINT analogs are characterized with respect to their structural integrity, physical and chemical stability.

Structural analysis of proteins includes assessment of secondary structure by far-UV CD. Aproximately 100 $\mu$l of 1 mg/ml FLINT analog solution in phosphate buffer, pH 7.4 is used in a scan from 240 to 180 nm in 0.5 nm steps, 1 nm bandwidth, with 3 sec time constant, an average of 3 scans in a 0.01 cm cell at room temperature. Near-UV CD spectra is taken from 240 to 350 nm, 0.5 nm step, 1 nm bandwidth, 5 second time constant, with average of 3 scans at room temperature. Analogs with similar spectra compared to native FLINT are preferred.

Intrinsic tryptophan fluorescence is measured with the following parameters: excitation through a 1 cm pathlength cell at 298 nm with a 2/2 nm slithwidth with emission collected from 305–400 nm with a 2/2 nm slithwidth, 05 nm step, through a 0.4 cm pathlength with 1 sec integration time. A "blue shift" is generally indicative that aromatic residues are more deeply buried in the protein structure and is often accompanied by improved pharmaceutical properties.

Quaternary structure of FLINT analogs can be examined by equilibrium sedimentation analysis performed in an ultracentrifuge with 3 mm width cells. Analogs with similar equilibrium sedimentation values compared to native FLINT are preferred.

Physical stability analysis includes examination of the propensity for aggregation of FLINT analogs as a reflection of their surface properties. Physical stability assays are described in the following paragraphs.

Dynamic Light Scattering Assay(DLS): A protein solution is diluted into either a) PBS, pH 7.4, b) PBS, 0.5 M NaCl, or c) PBS, pH 7.4 and 3 mg/mL m-Cresol, containing 0.1 to 5 mg/mL protein. The pH is adjusted to 7.4 (±0.05) with HCl/NaOH and filtered into a 6×50 mm borasilica type-I glass tube. The average light-scatter intensity weighted particle size is collected on a Brookhaven BI900 Instrument consisting of a goniometer at a 90° angle, digital correlator, and a Lexel model 3500 argon ion laser adjusted to the 488-nm line. The experimentally determined autocorrelation function C(t) is analyzed by the cumulants method to yield hydrodynamic diameter. The time before a significant change in particle size, or lag time, is determined by fitting linear lines to the pre-growth and growth phase data points. The intersection is defined as the lag time. Decreased light scattering by an analog compared with native FLINT at the same concentration and temperature is generally indicative that the analog aggregates to a lesser extent than native protein.

Differential scanning Callorimetry (DSC): Physical stability as reflected in the melting temperature (Tm) of the protein is determined by DSC (Differential Scanning Callorimetry). Usually FLINT analogs are scanned from 5°–100° C. with a 60° C./h scan rate and a 16 second filtering parameter. Higher melting temperatures are generally indicative of physical stability.

Chemical stability of FLINT analogs diluted to 0.5 mg/ml is monitored by reversed-phase HPLC analysis (RP-HPLC) and size exclusion chromatography. The reversed-phase method consists of an acetonitrile/TFA gradient system optimized for FLINT with detection at 214 nm using a Zorbax 300SB-C8 column at 40° C. The size exclusion method consists of a PBS mobile phase at pH 7.4 on a Superdex-75 (3.2×300 mm) column at room temperature. Changes in the reverse-phase chromatogram are generally indicative of chemical instability.

Example 11

In vivo testing of FLINT analogs for treatment of Liver Damage

Challenge with a low dose of lipopolysaccaride (LPS) induces acute and massive hepatic injury in rodents that can be used as a model of liver damage (See e.g. Tsuji H., et al, 1997, Infection and Immunity, 65(5):1892–1898). The activity of the FLINT anlogs of the present invention against acute liver failure was determined using a modification of the procedure reported by Tsuji et al., supra. Briefly, BALB/c mice (Harlan) were given intravenous injections in the lateral tail vein of 6 mg of D(+)-Galactosamine (Sigma, 39F-0539) in 100 $\mu$l of PBS (GIBCO-BRL), and 3 $\mu$g of Lipopolysaccharide B *E.coli* 026:B6 (LPS) (Difco, 3920-25-2) in 100 $\mu$l of PBS. After LPS challenge, the animals were injected intraperitoneally with a FLINT analog (200 $\mu$g). Suitable controls included hamster IgG (500 $\mu$g, Cappel, 30926), mAb against murine TNF, TN3-19.12 (500 $\mu$g, Sheehan K. C. F. et. al. J. Immunol. 1989. 142:3884), and Anti-mouse Fas Ligand (500 $\mu$g, PharMingen, MO24301) at 0, 2, 4, 6 hour-point respectively. The survival rates of the mice were determined 24 and 48 hours after LPS injection.

In one experiment, R218Q FLINT Fc was compared with FLINT produced in AV12 or CHO cells. In this experiment the R218Q FLINT Fc construct was as effective as FLINT in protecting animals from acute liver damage.

Example 12

In vivo testing of FLINT analogs for treatment of Septic Shock

To test the action of FLINT analogs in a septic shock model, a modification of the procedure in Example 10 is followed. The animals are given 200 $\mu$g of a FLINT analog at various time points after challenge with 200 $\mu$g of LPS. Without treatment, it is expected that such a dose of LPS would be lethal to the mice.

Example 13

FLINT Analog/FAS Ligand Binding Assay

The binding between FLINT analogs and Fas Ligand can be confirmed and binding affinities determined (e.g., kinetics, specificity, affinity, cooperativity, relative binding pattern, concentration) using real-time biomolecular interaction analysis (hereinafter BIACore). To monitor biomolecular interactions BIACore uses the optical phenomenon surface plasmon resonance. Detection depends on changes in the mass concentration of macromolecules at the biospecific interface.

Materials and Methods:
Biacoree®2000 device (Biacore AB, Rapsgatan 7, S-754 50 Uppsala, Sweden)
Sensor Chip CM5 (Biacore)
Amine coupling kit (Biacore)
Washing buffer: HBS-EP (Biacore)
Guanidine Isothiocyanate Solution (GibcoBRL)
Fas Ligand (Kamiya Biomedical Company, 910 Industry Drive, Seattle, Wash. 98188)
FLINT Analogs
Fas/Fc chimera (R&D Systems)

Immobilization Protocol

FasL or a FLINT analog is immobilized, through their primary amine group on the lysine residues onto carboxymethyldextran polymer attached to a gold surface within a flow chamber (Sensor Chip CM5). Immobilization is carried out using the amine coupling kit (Biacore) according to manufacturer's protocols. Briefly, 100 µl of either FasL or FLINT analog in solution (10–25 µg/ml in sodium acetate buffer 20 mM, pH 5.0) is loaded onto an activated CM5 chip. After coupling, excess reactive groups on the surface are deactivated with 1M ethanolamine hydrochloride pH8.5. The chip is then washed with the sodium acetate buffer 20 mM, pH5.0 to remove non-covalently bound material.

Interaction Analysis:

To analyze the interactions between FasL and FLINT analogs, solutions containing the FLINT analogs are passed over the chip with Fas Ligand immobilized thereon. The amount of FLINT analog associated with FasL is determined using a surface plasmon resonance signal (in response units, RU). Typically, a FLINT analog solution (different concentrations in HBS-ET buffer) is loaded on a sensor chip for 10 minutes at a flow rate of 5 µl/min. The chip is then washed with HBS-ET buffer (10 mM Hepes, pH7.4; 150 mM NaCl, 3 mM EDTA, 0.005% Surfactant P20) for 2 minutes at a flow rate of 5 µl/min.

To further analyze interactions between FLINT analogs and FasL, solutions containing FasL are passed over the chip with FLINT analog immobilized thereon. The amounts of FasL associated with the FLINT analog is determined using a surface plasmon resonance signal (in response units, RU). The protocol of loading, washing and regeneration of Flint bioactive chip is as described above for the FasL chip.

Determination of Affinity Constants
Experimental data is evaluated and binding parameters determined using BIACore evaluation 3.0.2 software (Biacore).

Example 14

FLINT Analogs With Surface Accessible N-Glycosylation Sites

A three dimensional model of FLINT was obtained by homology modeling. Using the program SEQFOLD, (Molecular Simulations Inc. San Diego, Calif.), FLINT was found to have a significant sequence homology to ltnr from the protein data bank (1tnr.pdb from Brookhaven National Laboratory, Upton, N.Y.). The identity between FLINT and the Tumor Necrosis Factor Receptor I was found to be about 30% over the range of 133 amino acids of FLINT at the N-terminus. Using the program BLAST, the identity was calculated to be about 36% and the homology to be about 50%.

Using the program MODELER, (available through Molecular Simulations Inc., San Diego, Calif.), several homology models were built and the one having the best profile score was selected as the final model. The profile score for the best model was 28.3, whereas the profile score for the template crystal structure was 29.2. The model was also verified with the template structure for the proper disulfide bonds.

Similarly, TNF-beta was selected as having the best homology with FasL and a model was constructed, as described above for FLINT. FasL was found to have about 30% identity to TNF-Beta and the profile score for the model was 29.2, whereas the profile score for TNF-Beta was 39.5.

Three dimensional models for FLINT and FasL were complexed together in similar fashion to the known crystal structure of tumor necrosis factor (p55) in complexation with TNF-Beta (reported in 1tnr.pdb). This model was minimized to remove nonbonded short contacts. The final model of the complex was used for further analysis.

FLINT analogs having new N-glycosylation sites can be obtained by replacing with asparagine the following amino acid residues: at positions 12, 34 (together with replacement of residue 36 with threonine), 35, 132 and 194.

The computer and homology modeling described above predicts that the new N-glycosylation sites are exposed at the surface of the molecule. Therefore, the new sites are likely to be glycosylated. The modeling also showed that the new glycosylation sites are located far enough from the site at which FLINT binds FAS Ligand so that the affinity of the analogs for FAS Ligand is unlikely to be adversely affected by glycosylation of the FLINT analogs.

Example 15

Analysis of FLINT Analogs Containing Additional Glycosylation Sites

Mass Spectrometry and HPLC profiling of fluorescence labeled oligosaccharides can be used to analyze FLINT analogs. For HPLC profiling of fluorescence labeled oligosaccharides 50 to 100 ug of FLINT analog is reduced by DTT. This material is then alkylated by iodoacetic acid. The N-linked oligosaccharides from the analog are removed by N-glycosidase F. The protein is precipitated by acetic acid. The cleaved oligosaccharides are then labeled with 2-amino benzamide and subjected to HPLC profiling on a weak ion exchanger. Similar methods are described in Methods in Molecular Biology series, vol. 14, Glycoprotein Analysis in Biomedicine, edited by Elizabeth F. Hounsell, 1993, the entire teachings of which are incorporated here in by reference.

Example 16

Production of the FLINT Metabolite

FLINT was purified from AV12 RGT 18 cells transfected with a recombinant vector carrying a FLINT cDNA (SEQ ID NO:1 or SEQ ID NO:3). This material was cleaved with thrombin at a weight ratio of 1 to 100 (thrombin to FLINT) for three hours at room temperature, dialyzed against 20 mM MOPS, 0.1% CHAPS, pH 6.5, and passed over a SP,Sepharose column at a flow rate of 1 ml/min. The column was washed with buffer A (20 mM MOPS, 0.1% CHAPS, pH 6.5) until the absorbance returned to baseline. The bound metabolite (amino acids 1 to 218 of SEQ ID NO:1) was eluted with a linear gradient from 0 to 300 mM NaCl (in buffer A) developed over 10 min. followed by a linear gradient for 0.3 to 0.5 M (in buffer A). Fractions were analyzed by SDS-PAGE and mass spectrometry. Fractions containing only the FLINT metabolite (1–218) were pooled and concentrated in Millipore Ultrafree centrifugal filter. The concentrated metabolite (1–218) was again analyzed by SDS-PAGE and mass spectrometry to assess purity. N-terminal sequencing confirmed the identity of the purified material as FLINT metabolite (1–218).

Example 17

FLINT Metabolite Binds LIGHT

A competitive ELISA was performed to determine if FLINT metabolite binds Flag-tagged LIGHT. Plates were coated with 2 ug/ml FLINT. In separate wells, sLIGHT was incubated with BSA/PBS, FLINT metabolite, FLINT, or HVEM-Fc as a control. After a 30 minute incubation the mixtures were added to the wells coated with FLINT. Any free sLIGHT would bind to the FLINT coated on the plate. The amount of SLIGHT that bound FLINT was measured using a FLAG antibody at 1 ug/ml. Detection was achieved using a 1:1000 strep/HRP. The data showed that the metabolite bound LIGHT as well as FLINT.

Example 18

Large Scale R218Q FLINT-Fc(minus hinge) Polypeptide Purification and Biophysical Characterization Media containing R218Q FLINT-Fc(minus hinge) was concentrated in an Amicon ProFlux M12 tangential filtration 10X using an Amicon S3Y10 UF membrane. Media containing R218Q FLINT-Fc was adjusted to 0.5 M NaCl and 5 mM EDTA. The concentrated media was passed over a Protein A HiTrap column (Pharmacia, 5 ml column) at a flow rate of 5 ml/min. The column was washed with buffer A (PBS (1 mM potassium phosphate, 3 mM sodium phosphate), 0.5 M NaCl, pH 7.4) until the absorbence returned to baseline and the bound polypeptides were eluted with 100% buffer B (50 mM citric acid, 0.5 M NaCl pH 3.5). The eluted material was neutralized with 100 µl of 1 M Tris pH 8.0 per ml of elution buffer. Fractions containing R218Q FLINT-Fc were pooled and passed over a Superdex 75 (Pharmacia, 16/60) sizing column equilibrated with PBS, 0.5 M NaCl, 10% glycerol, pH 7.4, at a flow rate of 1 ml/min. Fractions containing R218Q FLINT-Fc were analyzed by SDS-PAGE. The N-terminal sequence of R218Q FLINT-Fc was confirmed on the purified polypeptide.

Equilibrium sedimentation analysis indicated that R218Q FLINT-Fc is a dimer of molecular weight about 130 kDa. Differential scanning calorimetry indicated that the R218Q FLINT-Fc construct exhibits increased conformational stability with a melting temperature about 10° C. higher than wild type FLINT (64° C. versus 54° C.). No change in average hydrodynamic diameter was observed for 24 hours at 37° C. at approximately 1 mg/ml protein by differential light scattering analysis.

Example 19

Expression of R218Q FLINT Immunoadhesins

R218Q and WT FLINT/Fc constructs were expressed in transiently transfected 293EBNA cells for purification. Transfections were carried out in 700 $cm^2$ roller bottles on confluent monolayers of 293EBNA cells grown in DMEM F12 (3:1), 5% FBS, 20 mM HEPES, 2mM L-Glutamine with 50 ug/ml G418. Transfection cocktails were prepared in Gibco's OptiMEM media, using 65 ug of plasmid DNA per roller bottle and Roche Molecular Biochemicals transfection reagent FuGene. Fourty eight hours post-transfection, monolayers were rinsed with PBS and switched to 100 ml of serum free medium (Hybritech). Cells were monitored for $CO_2$, glutamine and glucose levels, and were harvested every 24 hours for 10 days. Typical expression levels ranged from 2–5 ug/ml.

Equivalents

Those skilled in the art will recognize, or be able to ascertain, using no more than routine experimentation, many equivalents to the specific embodiments of the invention described herein. Such equivalents are intended to be encompassed by the following claims.

We claim:

1. An isolated FLINT analog consisting of residues 1–218 of SEQ ID NO:1.

2. An isolated FLINT analog consisting of residues 1–247 of SEQ ID NO:3.

3. An isolated FLINT analog comprising residues 1–218 of SEQ ID NO:1, said analog having a lower binding affinity for FasL than FLINT.

4. An isolated FLINT analog comprising residues 1–247 of SEQ ID NO:3, said analog having a lower binding affinity for FasL than FLINT.

5. An isolated nucleic acid sequence that encodes residues 1–218 of SEQ ID NO:1.

6. An isolated nucleic acid sequence of claim 5 wherein said sequence comprises residues 1–654 of SEQ ID NO:2.

* * * * *